United States Patent
Sugiyama et al.

(10) Patent No.: US 7,175,613 B2
(45) Date of Patent: Feb. 13, 2007

(54) ABSORPTIVE PRODUCT HAVING REMOVABLE ABSORBERS

(75) Inventors: Katsuhiko Sugiyama, Kasugai (JP); Rie Kuwabara, Tokyo (JP); Migaku Suzuki, Tokyo (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/394,070

(22) Filed: Mar. 21, 2003

(65) Prior Publication Data
US 2003/0220623 A1 Nov. 27, 2003

Related U.S. Application Data

(63) Continuation of application No. PCT/JP01/08180, filed on Sep. 20, 2001.

(30) Foreign Application Priority Data

Sep. 21, 2000 (JP) .............................. 2000-287004
Mar. 6, 2001 (JP) .............................. 2001-062419

(51) Int. Cl.
*A61F 13/15* (2006.01)
*A61F 13/20* (2006.01)

(52) U.S. Cl. ........................ 604/385.14; 604/385.101; 604/385.01

(58) Field of Classification Search ................ 604/358, 604/378–384, 385.01, 385.101, 385.11, 385.13, 604/385.14
See application file for complete search history.

(56) References Cited

U.S. PATENT DOCUMENTS

| | | | |
|---|---|---|---|
| 833,849 A | 10/1906 | Schiff | |
| 1,695,109 A | 12/1928 | Kosloff | |
| 1,893,745 A | 1/1933 | Josias | |
| 2,468,445 A | 4/1949 | Hurst | |
| 2,476,585 A | 7/1949 | Cohen | |
| 2,530,647 A | 11/1950 | Buchler | |
| 2,574,279 A | 11/1951 | Oberle | |
| 2,688,328 A | 9/1954 | Marcus | |
| 2,826,199 A | 3/1958 | Brandon | |
| 2,832,346 A | 4/1958 | Morstad | |
| 2,842,129 A | 7/1958 | Ernstorff | |
| 2,868,205 A | 1/1959 | Epstein | |
| 3,050,063 A | 8/1962 | Margraf | |
| 3,162,196 A | 12/1964 | Salk | |
| 3,306,293 A | 2/1967 | Marder et al. | |
| 3,595,235 A | 7/1971 | Jespersen | |
| 3,658,064 A | 4/1972 | Pociluyko | |
| 3,771,524 A | 11/1973 | Ralph | |
| 3,848,594 A | 11/1974 | Buell | |

(Continued)

FOREIGN PATENT DOCUMENTS

CN 2073744 U 3/1991

(Continued)

*Primary Examiner*—Michele Kidwell
(74) *Attorney, Agent, or Firm*—Michael P. Hayden; Jay A. Krebs; Ken K. Patel

(57) ABSTRACT

An absorptive product comprising a front region, a rear region, a crotch region, a waist opening, a pair of leg openings, and a liquid-impermeable back sheet. Disposed interiorly of the back sheet are a front absorber and a rear absorber. An access port is provided for taking out and/or replacing at least one of these absorbers.

25 Claims, 22 Drawing Sheets

U.S. PATENT DOCUMENTS

| | | | |
|---|---|---|---|
| 3,860,003 A | 1/1975 | Buell | |
| 3,886,941 A | 6/1975 | Duane et al. | |
| 3,926,189 A | 12/1975 | Taylor | |
| 4,019,517 A | 4/1977 | Glassman | |
| 4,022,210 A | 5/1977 | Glassman | |
| 4,072,150 A | 2/1978 | Glassman | |
| 4,081,301 A | 3/1978 | Buell | |
| 4,257,418 A | 3/1981 | Hessner | |
| 4,260,443 A | 4/1981 | Lindsay et al. | |
| 4,265,245 A | 5/1981 | Glassman | |
| 4,326,302 A | 4/1982 | Lowe et al. | |
| 4,467,012 A | 8/1984 | Pedersen et al. | |
| 4,496,360 A | 1/1985 | Joffe et al. | |
| 4,515,595 A | 5/1985 | Kievit et al. | |
| 4,560,381 A | 12/1985 | Southwell | |
| 4,578,073 A | 3/1986 | Dysart et al. | |
| 4,597,760 A | 7/1986 | Buell | |
| 4,597,761 A | 7/1986 | Buell | |
| 4,615,695 A | 10/1986 | Cooper | |
| 4,625,001 A | 11/1986 | Tsubakimoto et al. | |
| 4,654,039 A | 3/1987 | Brandt et al. | |
| 4,666,983 A | 5/1987 | Tsubakimoto et al. | |
| 4,695,278 A | 9/1987 | Lawson | |
| 4,710,188 A | 12/1987 | Runeman | |
| 4,715,918 A | 12/1987 | Lang | |
| 4,770,656 A | 9/1988 | Proxmire et al. | |
| 4,773,903 A | 9/1988 | Weisman et al. | |
| D298,566 S | 11/1988 | Runeman | |
| 4,808,178 A | 2/1989 | Aziz et al. | |
| 4,816,025 A | 3/1989 | Foreman | |
| 4,834,736 A | 5/1989 | Boland et al. | |
| 4,834,737 A | 5/1989 | Khan | |
| 4,834,738 A | 5/1989 | Kielpikowski et al. | |
| 4,851,069 A | 7/1989 | Packard et al. | |
| 4,872,871 A | 10/1989 | Proxmire et al. | |
| 4,892,598 A | 1/1990 | Stevens et al. | |
| 4,923,454 A | 5/1990 | Seymour et al. | |
| 4,938,756 A | 7/1990 | Salek | |
| 4,950,264 A | 8/1990 | Osborn, III | |
| 4,961,736 A | 10/1990 | McCloud | |
| 4,964,860 A | 10/1990 | Gipson et al. | |
| 4,968,312 A | 11/1990 | Khan | |
| 4,988,344 A | 1/1991 | Reising et al. | |
| 4,988,345 A | 1/1991 | Reising | |
| 4,994,037 A | 2/1991 | Bernardin | |
| 5,009,650 A | 4/1991 | Bernardin | |
| 5,009,653 A | 4/1991 | Osborn, III | |
| 5,061,259 A | 10/1991 | Goldman et al. | |
| 5,069,672 A | 12/1991 | Wippler et al. | |
| 5,102,597 A | 4/1992 | Roe et al. | |
| 5,128,082 A | 7/1992 | Makoui | |
| 5,147,345 A | 9/1992 | Young et al. | |
| 5,149,335 A | 9/1992 | Kellenberger et al. | |
| 5,167,655 A | 12/1992 | McCoy | |
| 5,176,668 A | 1/1993 | Bernardin | |
| 5,181,915 A | 1/1993 | Smith | |
| 5,188,624 A | 2/1993 | Young, Sr. et al. | |
| 5,207,662 A | 5/1993 | James | |
| 5,207,663 A | 5/1993 | McQueen | |
| 5,217,445 A | 6/1993 | Young et al. | |
| 5,236,428 A | 8/1993 | Zajaczkowski | |
| 5,260,345 A | 11/1993 | DesMarais et al. | |
| 5,268,224 A | 12/1993 | DesMarais et al. | |
| 5,318,554 A | 6/1994 | Young et al. | |
| 5,324,561 A | 6/1994 | Rezai et al. | |
| 5,325,543 A | 7/1994 | Allen | |
| 5,358,500 A | 10/1994 | LaVon et al. | |
| 5,360,422 A | 11/1994 | Brownlee et al. | |
| 5,383,867 A | 1/1995 | Klinger | |
| 5,387,207 A | 2/1995 | Dyer et al. | |
| 5,401,266 A | 3/1995 | Runeman et al. | |
| 5,405,342 A | 4/1995 | Roessler et al. | |
| 5,409,476 A | 4/1995 | Coates | |
| 5,458,591 A | 10/1995 | Roessler et al. | |
| 5,476,457 A | 12/1995 | Roessler et al. | |
| 5,486,168 A | 1/1996 | Runeman et al. | |
| 5,531,728 A | 7/1996 | Lash | |
| 5,549,589 A | 8/1996 | Horney et al. | |
| 5,550,167 A | 8/1996 | DesMarais | |
| 5,556,393 A | 9/1996 | Rönnberg | |
| 5,563,179 A | 10/1996 | Stone et al. | |
| 5,569,229 A | 10/1996 | Rogers | |
| 5,613,959 A | 3/1997 | Roessler et al. | |
| 5,624,422 A | 4/1997 | Allen | |
| 5,636,387 A | 6/1997 | Lundy | |
| 5,650,222 A | 7/1997 | DesMarais et al. | |
| 5,800,416 A | 9/1998 | Seger et al. | |
| 5,817,081 A | 10/1998 | LaVon et al. | |
| 5,827,253 A | 10/1998 | Young et al. | |
| 5,843,055 A | 12/1998 | Seger | |
| 5,843,065 A | 12/1998 | Wyant | |
| 5,906,602 A | 5/1999 | Weber et al. | |
| 6,015,935 A | 1/2000 | LaVon et al. | |
| 6,083,210 A | 7/2000 | Young et al. | |
| 6,123,692 A | 9/2000 | Guidotti et al. | |
| 6,229,061 B1 | 5/2001 | Dragoo et al. | |
| 6,336,923 B1 | 1/2002 | Fujioka et al. | |
| 6,793,649 B1 | 9/2004 | Fujioka et al. | |
| 2002/0013566 A1 | 1/2002 | Chappell et al. | |
| 2002/0058921 A1 | 5/2002 | Chappell et al. | |
| 2002/0091368 A1 | 7/2002 | LaVon et al. | |
| 2002/0143316 A1 | 10/2002 | Sherrod et al. | |
| 2003/0199844 A1 | 10/2003 | LaVon et al. | |
| 2004/0024379 A1 | 2/2004 | LaVon et al. | |
| 2004/0030314 A1 | 2/2004 | LaVon et al. | |
| 2004/0039361 A1* | 2/2004 | LaVon et al. | 604/385.01 |

FOREIGN PATENT DOCUMENTS

| | | |
|---|---|---|
| EP | 0319 314 A2 | 6/1989 |
| GB | 493819 | 10/1938 |
| GB | 734994 | 8/1955 |
| GB | 1 411 087 | 10/1975 |
| GB | 2 042 342 | 9/1980 |
| GB | 2 269 998 | 3/1994 |
| GB | 2 295 321 A | 5/1996 |
| GB | 2 296 441 A * | 7/1996 |
| JP | 63-184012 | 11/1988 |
| JP | 1993-86314 | 11/1993 |
| JP | 6121812 | 5/1994 |
| WO | WO 91/10413 | 7/1991 |
| WO | WO 91/16871 | 11/1991 |
| WO | WO 95/17870 | 7/1995 |
| WO | WO 01/60300 A1 | 8/2001 |

* cited by examiner

ABSORPTIVE PRODUCT HAVING REMOVABLE ABSORBERS

CROSS-REFERENCE TO RELATED APPLICATION

This application is a continuation application of prior copending International Application No. PCT/JP01/08180, filed Sep. 20, 2001, designating the U.S.

FIELD OF THE INVENTION

The present invention relates to an absorptive product which has removable absorbers which can be removed while being worn, wherein said removable absorbers are classified according to function as absorbers for either urine or feces, and where the absorber for feces in particular is prevented from adhering to the wearer.

BACKGROUND OF THE INVENTION

In this specification, the terminology "absorptive product" is used to include products which handle all forms of feces or urine, including diapers for nursing infants or caregivers, as well as incontinence products for adults.

According to a report entitled "Diaper Rash Phenomenon" by Kazuya Yamamoto in pages 949 through 956 of "Dermatology 30 (1998)", the cause and occurrence mechanism of diaper rash is that, (i) ammonia is generated by a mixture of urine and feces, (ii) the ammonia creates an alkaline environment, (iii) enzymes in the feces are strongly activated in the alkaline environment, (iv) these enzymes and ammonia create inflammation in areas where the skin is weak, causing diaper rash. It was pointed out that weak areas of the skin are caused by mechanical stimulation when the materials which comprise the diaper contact the skin, or where the humid environment inside of the diaper causes the skin to become swollen.

The causes of diaper rash explained above are being eliminated by improved performance relating to advancement in the technology of super-absorbent polymer materials. For instance, by rapidly absorbing urine and minimizing dispersion after urination, it has become possible to minimize mixing with feces even if there has been excretion. Furthermore, by using a gas permeable sheet, the stuffy conditions inside the diaper are relieved, which is effective in preventing swelling of the skin. Because of advancements of these countermeasures for diaper rash, occurrences of skin problems such as rashes arising from the use of so-called disposable diapers are becoming less prevalent.

However, if the urine and feces are excreted at about the same time, these countermeasures are still inadequate for preventing inflammation when the stools are soft. For soft stools in particular, even if the feces and urine do not mix, there will be a significant negative affect on the skin if left unattended. This is because soft stools do not easily pass through the top sheet of the diaper that is in contact with the skin, so that while a portion of the liquid content moves to the absorber, the stool remaining on the top sheet adheres to the buttocks of the wearer. Therefore, although there will be no skin problems, cleanup of the buttocks will be difficult when the diaper is changed.

Therefore, in order to prevent the mixing of feces and urine, and also to prevent the adherence of feces to the buttocks, a diaper is proposed which is constructed such that openings are made in the top sheet and the skin contact sheet of the diaper so that the feces can be moved to the outside, and the urine and feces can remain separated. However, because there is no mechanism to maintain the configuration of the top sheet or the skin contact sheet, depending upon the position the diaper is worn, it is difficult to maintain these openings in an open configurration.

In order to resolve these problems, diapers which separate the urine and the feces have been proposed in (a) Tokkai S61-41304 Official Bulletin, (b) Jikkai H6-5614 Official Bulletin, (c) Jikkai H6-11723 Official Bulletin, (d) Utility Model Registration 2559050 Official Bulletin, and (e) Tokuhyo H10-513072 Official Bulletin.

The diaper disclosed in (a) Tokkai S61-41304 Official Bulletin has a long opening at the center of the top sheet running in the lengthwise direction, and by adding an elastic material along the edge of the opening, the top sheet can be made firm so that the opening does not close.

The diaper disclosed in (b) Jikkai H6-5614 Official Bulletin has a concave section extending from below an opening in the top sheet, and a valve which extends the top sheet from the perimeter of the opening to the center area such that the separated feces is prevented from returning by the opening.

The diaper disclosed in (c) Jikkai H6-11723 Official Bulletin has a first top sheet overlying a second top sheet, and there are several elastic members so that the opening which is formed in the center region of and running in the lengthwise direction of the second top sheet is pulled open in the widthwise direction.

The disposable diaper disclosed in (d) Utility model registration 2559050 Official Bulletin with an absorbent panel between a liquid permeable inner sheet and a liquid non-permeable outer sheet, has a second liquid permeable inner sheet which overlies the first liquid permeable inner sheet and has openings facing the anus and the urinary organs of the wearer, and also has a space formed between these two inner sheets.

The disposable absorptive product disclosed in (e) Tokuhyo H10-513072 Official Bulletin has a hole facing the anus and/or the urinary organs of the wearer, and the absorbent material is formed with a pocket to receive the stool or urine.

However, the prior art shown above also has the following problems.

For the diapers shown in (a) Tokkai S61-41304 Official Bulletin and (b) Jikkai H6-5614 Official Bulletin, when observations on their actual use were made, it was seen that the crotch region of the diaper would be shifted toward the center by both thighs of the wearer, and would hang down rather than contact the skin. In other words, with these diapers a problem occurred where, because the crotch portion of the top sheet or surface sheet (hereafter referred to as "top sheet") was not in tight contact with the crotch of the wearer, the opening made in the top sheet was not effective, and the feces would be spread out across the top of the top sheet. Even if the position of the opening in the top sheet and the anus of the wearer were in line with each other, the opening would be a closed condition because the top sheet was not in close contact with the crotch of the wearer, and it is thought that the feces could not be directed between the top sheet and the back sheet through the opening.

The diaper disclosed by (c) Jikkai H6-11723 Official Bulletin also has a similar problem where the opening is only opened in the widthwise direction, so depending on the way that it is worn, the opening may be forced closed, and fundamentally, the function of the opening cannot be sufficiently shown.

Also, with the disposable diaper disclosed in (d) Utility model registration 2559050 Official Bulletin, while adhesion of urine and feces to the buttocks region can be minimized, the mixing of urine and feces cannot be prevented, and the contamination of the buttocks region by these products cannot be eliminated.

Furthermore, when disposing of stools with the disposable absorptive product disclosed in (e) Tokuhyo H10-513072 Official Bulletin, it is necessary to dispose of the whole disposable absorptive product, and if urine has not been excreted, the urine absorbing function cannot be effectively used and is disposed of as well. These types of problems are applicable to any of the above mentioned conventional diapers.

SUMMARY OF THE INVENTION

The purpose of the present invention is to provide an absorptive product where the urine and stools can be handled separately, skin problems like diaper rash which are caused by the feces are minimized, and where the feces alone can easily be disposed without getting the hands dirty.

Another purpose of the present invention is to provide an absorptive product which is constructed such that at least a portion of the absorber can be removed while being worn, so that after the absorber has been contaminated by excretion, it can be replaced with a new absorber. This type of absorptive product can reduce the amount of labor for the caregiver, as well as reduce the cost associated with using the diaper and control the total quantity of garbage generated as compared to disposing of the whole absorptive product when contaminated by excretion.

With the present invention, an absorptive product can be provided comprising a front region, a rear region, and a crotch region, as well as a single opening around the waist and a pair of openings around the legs, a back sheet constructed from a liquid-impermeable sheet, and absorbers arranged interiorly of said back sheet, wherein said absorbers comprise of at least one of a front absorbers which extends from said front region to said crotch region and primarily absorbs urine, and a rear absorber which extends from said crotch to said rear region and primarily retains the feces, and for at least one of said front absorbers or said rear absorber is constructed to be removable with regard to said back sheet, and furthermore said absorptive product has an access port where at least one of said front absorbers or said rear absorber can be removed from said absorptive product while said absorptive product is being worn.

It is preferable if the front absorber and the rear absorber are separated by a partition to prevent excretions from moving between the two. Furthermore, because the front absorber is made primarily for absorbing urine, it is preferable that it have the capacity to absorb large amounts of liquids in a short period of time. On the other hand, the rear absorber is primarily for retaining feces, so it does not need to have such a high capability of absorbing liquids.

In one form of embodiment of the present invention, an access port for removing the removable absorber from the back sheet is formed as a long narrow opening extending along the edge of the opening around the waist. This opening may be made by perforating the back sheet so that the opening can be opened by tearing the joint of this perforation line.

The front sheet and the back sheet may be constructed with separate liquid permeable sheets, liquid impermeable sheets, and an absorbent material which is retained between the two. For absorbent material, it is preferable to use materials which include pulp fiber or polymer absorbent materials.

The front absorber and the rear absorber may be made of materials which hydrolyze, but in this case it is easy to remove and dispose of the removable absorbent.

The rear absorber may be covered with a feces separating sheet which has an opening for separating the feces. The opening for separating the feces may have appropriate sized pores, or the opening may be a size which will permit the feces to pass through and have a net-like material which covers the whole surface.

The absorptive product of the present invention shall preferably have a means to control the position of the removable absorber in order to retain in the designated position.

With the absorptive product of the present invention, the removable absorber may be removed, and if desired, a new replacement absorber inserted even while being worn. This insertion operation may be further simplified by using an applicator.

DETAILED DESCRIPTION OF THE INVENTION

Figure 1A:
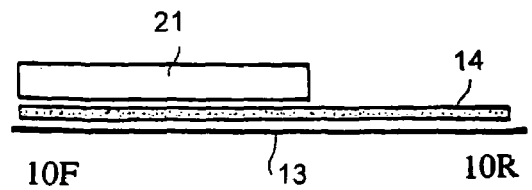
FIGS. 1 (*a*) through (*f*) are simple lengthwise cross section sketches showing the relationship between the multiple absorbers and the back sheet for an absorptive product which is constructed based on the fundamental concepts of the present invention.
Figure 1B:
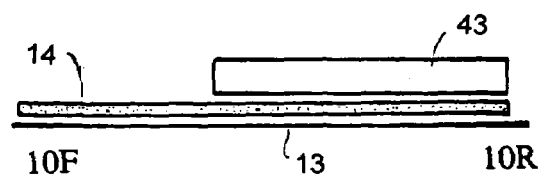
Figure 1C:
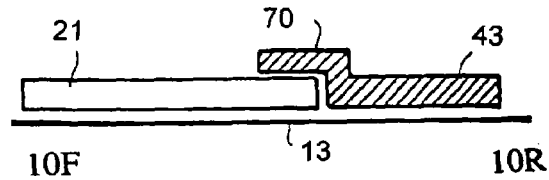
Figure 1D:
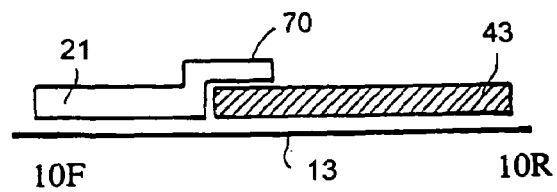
Figure 1E:
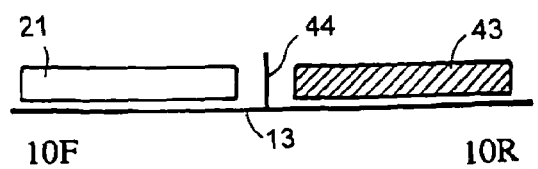
Figure 1F:
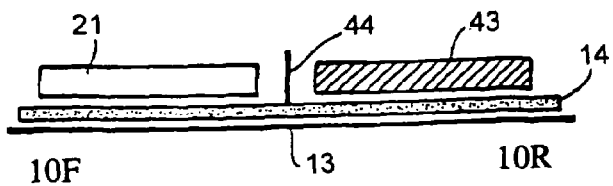
Figure 2A:
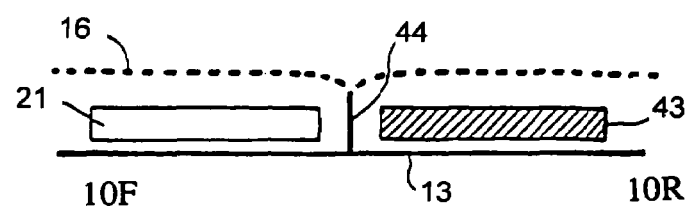
FIGS. 2 (*a*) through (*d*) are simple lengthwise cross section sketches which show examples of the partition construction between the front absorber and rear absorber for an absorptive product which is constructed based on the fundamental concepts of the present invention.
Figure 2B:
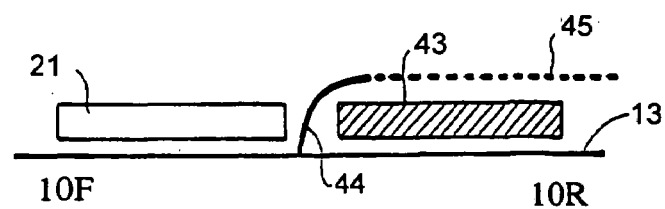
Figure 2C:
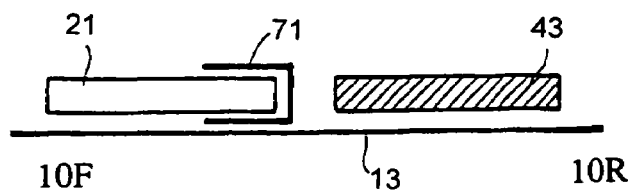
Figure 2D:
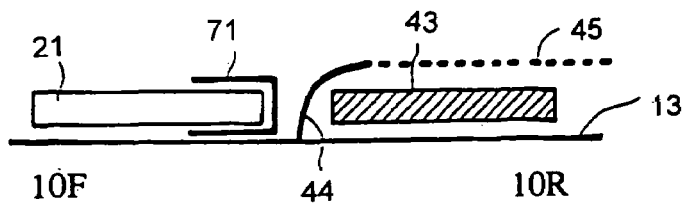

First, the fundamental concepts of the present invention will be described while referring to the Figures.

FIG. 1 (*a*) shows the first concept of the absorptive product of the present invention, and 21 refers to the front absorber which is in place primarily to absorb urine, 14 refers to a fixed absorber, and 13 refers to the back sheet. The front region of the absorptive product is identified by the reference numeral 10F and the rear region of the absorptive product is identified by the reference numeral 10R. The fixed absorber 14 is positioned to extend across a wide region reaching from the front region to the rear region interiorly of the back sheet 13, but as will be described in detail later, while the front absorber 21 is positioned to cover the appropriate area on the front region in line with its purpose to primarily absorb urine from the wearer, it is constructed to be able to be inserted or removed while the absorptive product is being worn.

With the alternate version shown in FIG. 1 (*b*), part of the front absorber 21 has been omitted, and the rear absorber 43 has been set adjacent to the front absorber 21 primarily to retain feces.

The most critical characteristic of the present invention is that it is constructed such that either one or both of the front absorber 21 and the rear absorber 43 are removable with regard to the back sheet 13.

With the alternate versions shown in FIGS. 1 (*c*) and (*d*), both front absorber 21 and rear absorber 43 are in place, and one of the two absorbers forms an overlap region 70 which extends to cover the edge of the other absorber. Also, with the alternate versions shown in FIGS. 1 (*e*) and (*f*), a partition 44 has been set as a separation means to restrict the movement of excretion products between the front absorber 21 and the rear absorber 43. In the example of FIG. 1 (*e*), the partition 44 is connected to the back sheet 13, and in the example of FIG. 1 (*f*) it is connected to the fixed absorber 14 which is on the back sheet 13.

In the concept shown in FIGS. 2 (*a*) through (*d*), a variant of the separation means is applied. In the example of FIG. 2 (*a*), a top sheet 16 which covers front absorber 21 and rear absorber 43 is connected to the top edge of the film-like partition 44 which is connected to the back sheet 13. In the example of FIG. 2 (*b*), a feces separator sheet 45 which covers rear absorber 43 is connected to the top edge of the film-like partition 44. In the example of FIG. 2 (*c*), this partition between the front absorber 21 and the rear absorber 43 is formed by a pocket-like trap 71 which covers the edge on the side of the front absorber 21 which is in close proximity to the rear absorber 43. In the example of FIG. 2 (*d*), a film-like partition 44 or a feces separator sheet 45 which is connected to the back sheet 13 is set in addition to the construction of FIG. 2 (*c*).

Figure 3A:
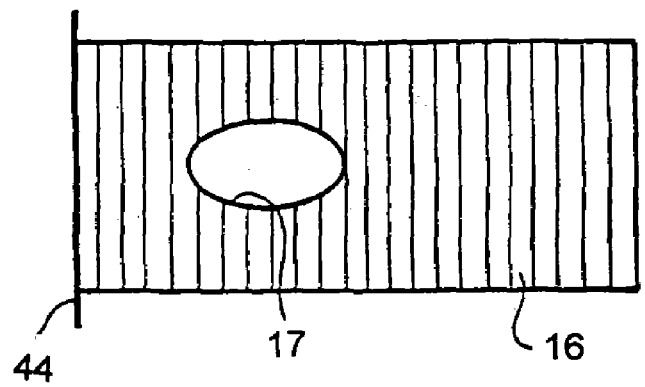
FIGS. 3 (*a*) through (*c*) are simple top view sketches which show examples of the construction of the feces separator for an absorptive product which is constructed based on the fundamental concepts of the present invention.
Figure 3B:
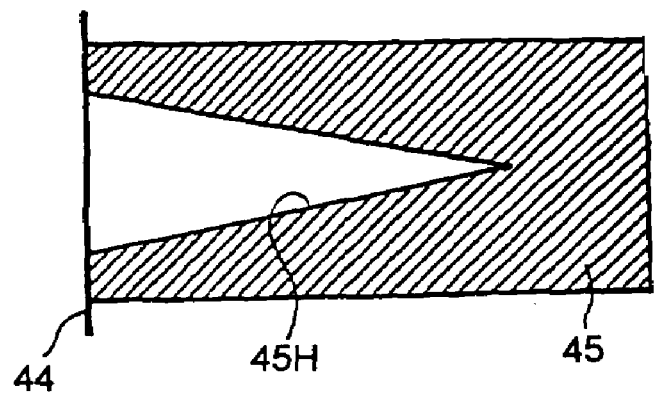
Figure 3C:
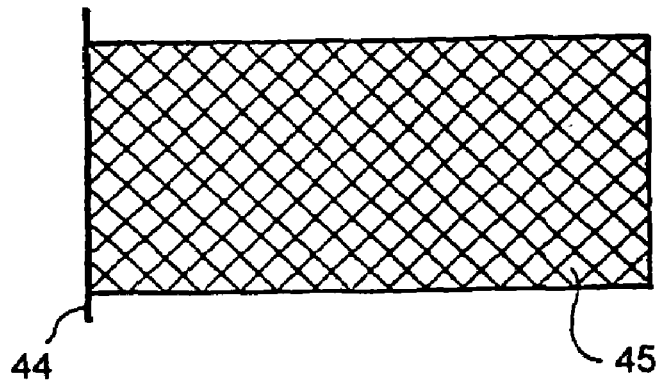

In another concept of the present invention shown in FIG. 3 (*a*), the top sheet 16 which is connected to the partition 44 has a feces separator opening 17 which is formed in a position which corresponds to the excretion area of the wearer. In this case, immediately after excretion, the feces can pass through the feces separator opening 17, moving downward without contacting the top sheet 16. FIG. 3 (*b*) shows an example where a cut 45H is made in the feces separator sheet 45 which is connected to the partition 44, and FIG. 3 (*c*) shows an example with a net-like feces separator sheet 45 which has pores large enough to be permeable to feces.

Figure 4A:
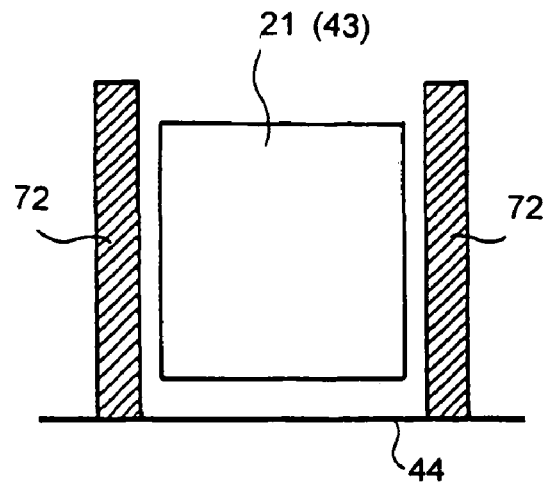
FIGS. 4 (*a*) through (*c*) are simple lengthwise cross section sketches which show examples of a structure to control the position of the removable absorber for an absorptive product which is constructed based on the fundamental concepts of the present invention.
Figure 4B:
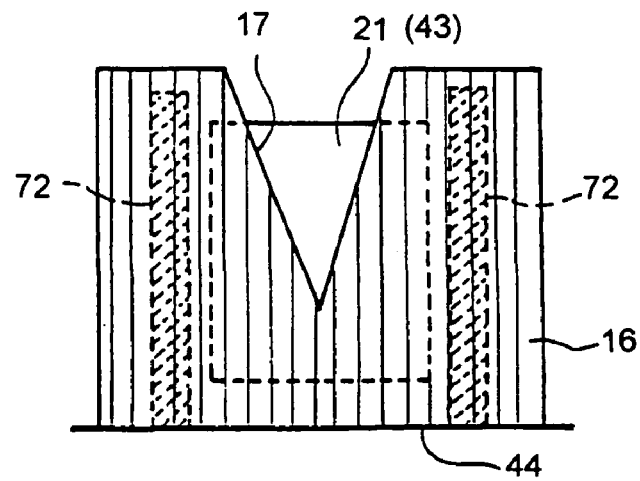
Figure 4C:
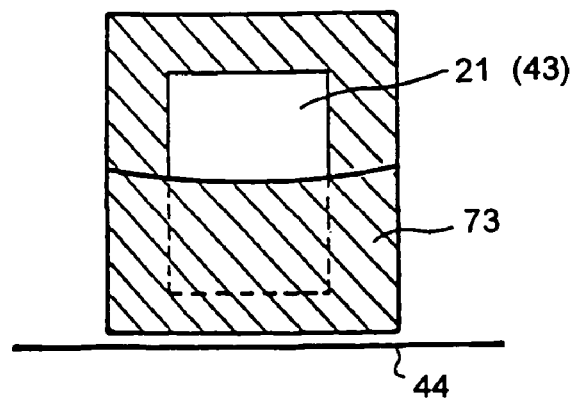

Furthermore, FIGS. 4 (*a*) through (*c*) show a position control means which retains the removable front absorber 21 or rear absorber 43 in the designated location relative to the back sheet 13. In the example of FIG. 4 (*a*), a pair of side banks 72 are set at an interval which can accommodate the front absorber 21 or the rear absorber 43, and the front absorber 21 or the rear absorber 43 is retained in the pocket-like retaining area formed by the partition 44 and the side banks 72. In the example of FIG. 4 (*b*), a top sheet 16 is set which has a feces separator opening 17, and said top sheet covers front absorber 21 and rear absorber 43 which are retained in the designated position between the pair of side banks 72, with regard to the construction shown in FIG. 2 (a). In the example of FIG. 4 (c), a bag-like capsule 73, made of PE film, for example, is secured in a designated position so that part of the front absorber 21 and the rear absorber 43 are exposed.

The concepts of the present invention have been briefly shown above, and concrete preferred embodiments will be described below.

Concrete preferred embodiments of the absorptive product of the present invention with a pull-on type, or in other words, a pants-type diaper construction will be described in detail while referring to Figures from FIG. 5 on. However, the present invention is not limited to these examples and other technologies which should be included in the summary of the present invention and which are shown in the claims of this disclosure can be applied.

With the open configuration for instance, applications of the present invention could of course include a tape-type diaper where the edges on both sides of the back sheet are extended in both directions to form side flaps and where the side edges of the side flaps are overlapped and fastened to the front region. Furthermore, washable cloth diapers could also be applicable, and in this case, only the removable absorber would be disposed of, and the other components like the back sheet and top sheet would be made of materials commonly used for underwear, like cotton, as well as polyester, nylon, rayon, silk, and blends of these materials with cotton.

Figure 5:
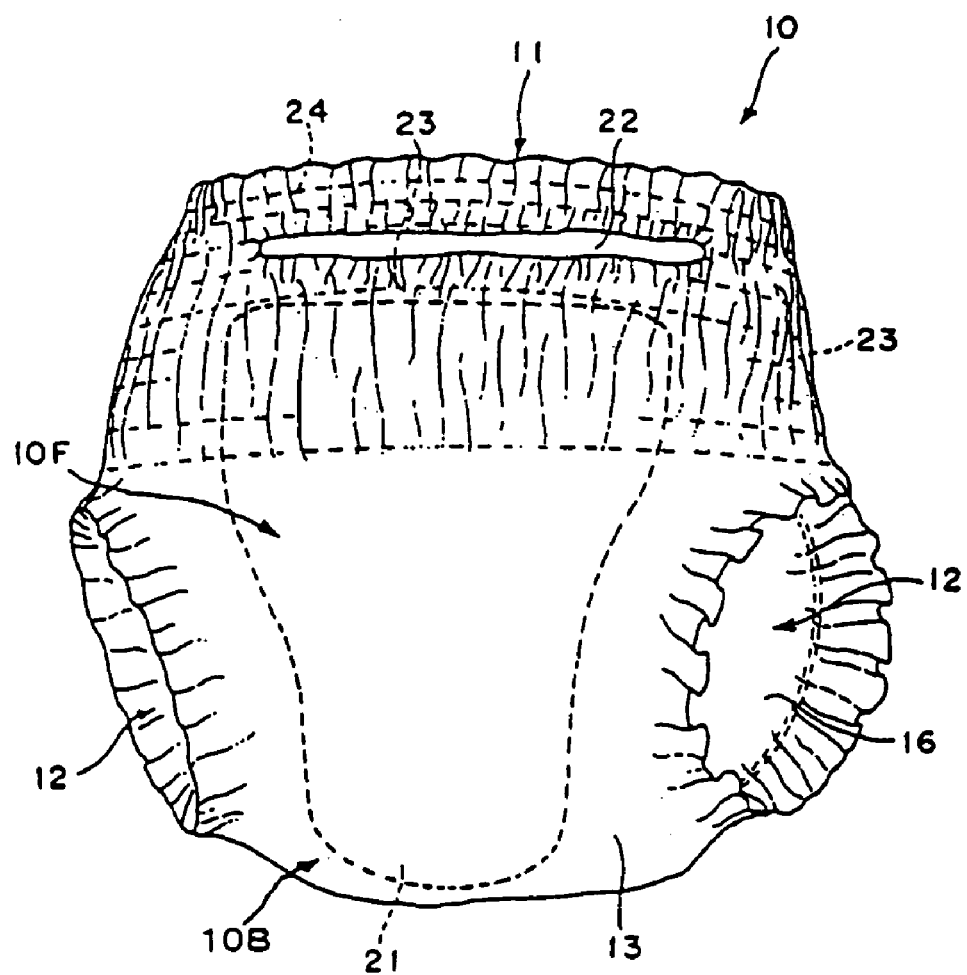
FIG. 5 is a perspective view which shows the appearance of an exemplary pants-type diaper form of an absorptive product of the present invention.
Figure 6:
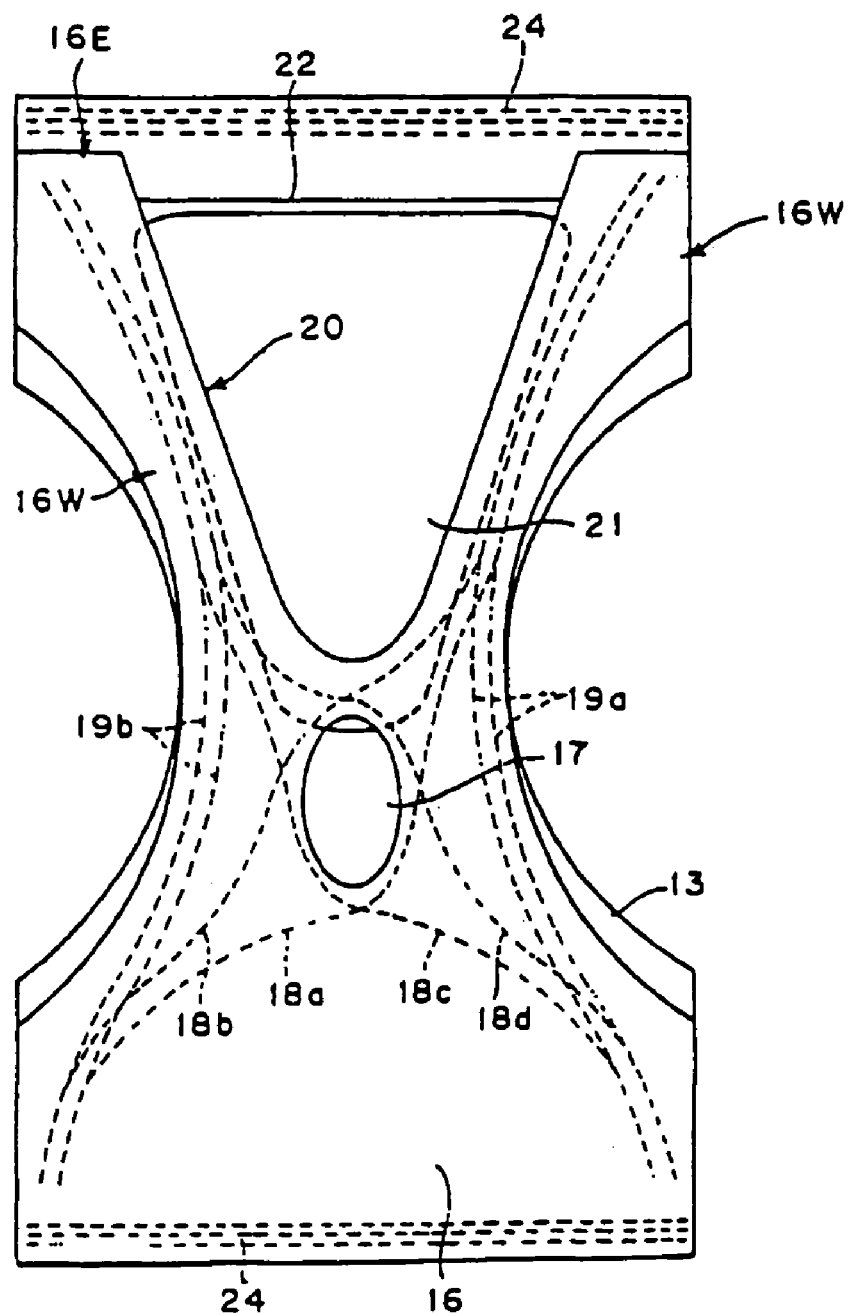
FIG. 6 is a plan view showing the interior of the absorptive product shown in FIG. 5.
Figure 7:
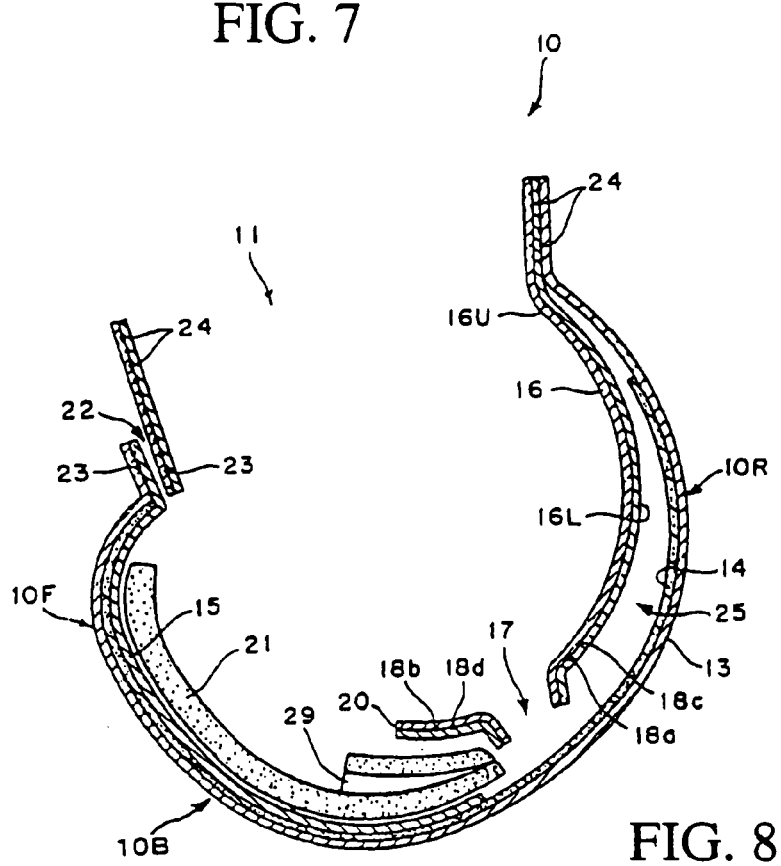
FIG. 7 is a cross section view along the line which runs from the front region through the crotch region to the rear region of the absorptive product shown in FIG. 5.

The appearance of an absorptive product which is the first preferred embodiment of the present invention is shown in FIG. 5, the open view is shown in FIG. 6, and a cross section drawing cut along the center from the front region 10F to the rear region 10R is shown in FIG. 7.

In other words, the absorptive product 10 of this embodiment is a pants-type product comprising an opening around the waist 11, a liquid impermeable back sheet 13 which forms a pair of openings around the legs 12, a sheet-type fixed absorber 14 which extends from the front region 10F to the rear region 10R and is located on said back sheet 13, a liquid permeable cover sheet 15 which is hydrophilic and is connected to the back sheet 13 so that said fixed absorber 14 is sandwiched to the back sheet 13 in the front region 10F, and a top sheet 16 which is positioned on the cover sheet 15 and the back sheet 13 and extends from the front region 10F to the rear region 10R and which is fastened to the cover sheet 15 and the back sheet 13 along the lengthwise side edges 16E and the widthwise side edges 16W.

In the center region of said top sheet 16, a feces separator opening 17 is formed in the crotch region 10B of the absorptive product 10 and in order to cover said feces separator opening 17, two sets of elastic members each comprising two elastic members 18a, 18b, 18c, 18d are positioned and fastened in the extended condition along the lengthwise direction of the top sheet 16, and also, a pair of elastic members 19a, 19b are positioned and fastened in an extended condition along the widthwise side edges 16W of the top sheet 16, or in other words, along the pair of openings around the legs 12.

A near V-shaped or near U-shaped cut 20 is made in the top sheet 16 in the center region in the widthwise direction of the front region 10F, and the front absorber 21, which has a receiving area, has a size which nearly covers all of said cut 20 and is sandwiched between the fixed absorber 14 and the top sheet 16.

Said front absorber 21 will be described in detail later. Furthermore, in the front region 10F, an opening to remove the front absorber 21, or in other words, a front access port 22 is formed in the back sheet 13 extending along the edge of the opening around the waist 11. Said front access port 22 can also be used to insert a new front absorber 21 if necessary after the used front absorber 21 has been removed.

Several strips of elastic material 23 are positioned in the region near the front access port 22 between the back sheet 13 and the top sheet 16 or the cover sheet 15 in the extended condition running along the front access port 22, as well as several strips of elastic material 24 around the waist which are between the back sheet 13 and the top sheet 16 or the cover sheet 15 in the extended condition running along the opening around the waist 11.

In this embodiment, the back sheet 13, which functions as an absorptive product cover, may also be a separate liquid impermeable sheet, or may even be a multi-layer sheet of several non-woven materials. For the liquid impermeable sheet, a humidity permeable liquid impermeable sheet, like a liquid impermeable polyethylene sheet or preferably a polyethylene sheet with holes in order to be gas permeable or an extended sheet made of a thermoplastic resin with a filler added, is preferable due to the fact that it can provide a more comfortable absorptive product because it is expected that dampness will be controlled by the humidity permeable properties.

For the above-mentioned liquid impermeable sheet, woven or knitted cloth may be used. The material used for said cloth may be material commonly used for underwear like cotton, polyester, nylon, rayon, for silk, as well as blends of these materials with cotton. If washable cloth is desired, it is preferable to use materials which are both water resistant and gas permeable like GORE-TEX (product name, made by W. L. Gore and Associates) which is processed with TEFLON (product name, made by DuPont), or MICROTEX (product name, made by Nitto Denko).

The top sheet 16 in this embodiment is made by overlaying an upper sheet 16U and a liner sheet 16L, and previously mentioned two sets of elastic members 18a, 18b, 18c, 18d as well as 19a, 19b are sandwiched between the upper sheet 16U and the liner sheet 16L. One set of elastic members 18a, 18b is positioned from one of the width sides of the front region 10F through the crotch region sandwiching the feces separator opening and extending to the other width side of the rear region 10R. The other set of elastic material 18c, 18d, is positioned from the other width side of the front region 10F through the crotch region sandwiching the feces separator opening and extending to the first width side of the rear region 10R. In other words, the two sets of elastic members 18a, 18b, 18c, 18d extend from two of the corners of the top sheet across to the corner situated on the diagonal in a manner such that they mutually intersect, sandwiching the feces separator opening 17 to form an X-shape configuration, and therefore the feces separator opening 17 is surrounded by the two sets of elastic members 18a, 18b, 18c, 18d. The feces separator opening 17 is in a lengthwise oblong shape in FIG. 6, but a widthwise oblong shape is also acceptable. However, because the feces passes through the top sheet and moves at an angle, the lengthwise configuration is more stable for separating the feces.

As can be clearly seen from FIG. 7, elastic members 18a, 18b, 18c, 18d cause the top sheet 16 to be in a suspended shape with regard to the back sheet 13. Therefore, when being worn, the top sheet 16 is in close contact with the skin of the wearer, and forms a space 25 for storing the feces between the top sheet 16 and the back sheet 13. When the top sheet is made of a material which has high elasticity, it is possible for the suspended configuration to be achieved even if the elastic members 18a, 18b, 18c, 18d are omitted.

The material used to make the top sheet 16 may be a non-woven material, mesh sheet, or film made of synthetic fibers which use as a base material thermoplastic resins like polyethylene, polypropylene, polyester, but it is also acceptable to use cloth. As mentioned previously, materials commonly used for underwear like cotton, polyester, nylon, rayon, or silk, as well as blends of these materials with cotton may be used for the cloth. If the top sheet 16 is made of cloth, it is preferable to use meriyasu weaved knit material or sheets which have been stretched by needle punch processing, in order to increase the contact with the wearer's skin. Besides these, it is preferable to use materials which are both water resistant and air permeable like the above-mentioned GORE-TEX (product name) treated with TEFLON (product name) and MICROTEX (product name). If cloth is used for the top sheet 16, it is acceptable to position elastic materials around the feces separator opening 17 or to border the perimeter of the feces separator opening with an oblique edge cut in order to make a structure which is difficult to deform.

Elastic members 18a, 18b, 18c, 18d, 23, 24 may be made of flat rubber by forming natural rubber into a ribbon configuration, as well as thread rubber, urethane thread, elastic net or elastic film, may have any width or any diameter, may be stretched to any elongation, and can be assembled using any fastening means such as hot melt, heat seal, or ultrasonic fusion.

The elastic members which are positioned to surround the feces separator opening 17, direct the feces to between the top sheet and the top sheet, passing through the feces separator opening 17, thus keeping the buttocks of the wearer clean, which can result in reducing the occurrence of skin trouble.

Figure 8:
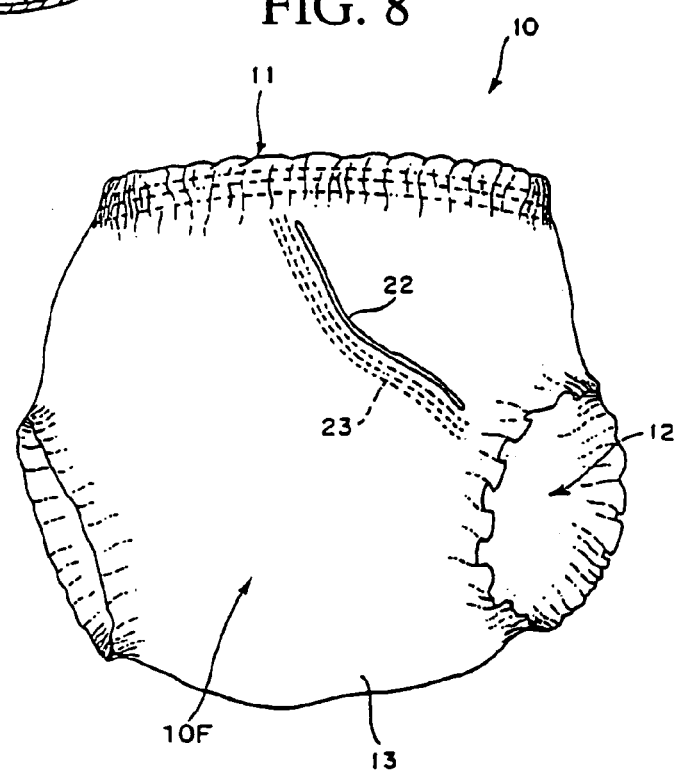
FIG. 8 is a perspective view which shows the appearance of another example of an absorptive product of the present invention.

An example where the position of the access port 22 in the back sheet 13 differs from the examples shown in FIGS. 5 through 7 is shown in FIG. 8. The access port 22 in this example is at the center in the height direction of the front region 10F of the absorptive product and is formed along an angled line from a position near the opening around the waist 11 to a position near the opening around one of the legs 12. Elastic member 23 is placed on the back sheet 13 on the crotch side of the access port 22, and therefore, the access port 22 can be easily opened.

With the access port 22 formed at an angle like this, it is an easy operation for the caregiver to put their arms around the wearer from the back and pull out the front absorber 21.

It is also possible for the access port 22 to be made with non-continuous slits or perforation line that can be torn to open the port. The appearance of this type of other embodiment of the present invention is shown in FIG. 9.

Figure 9:
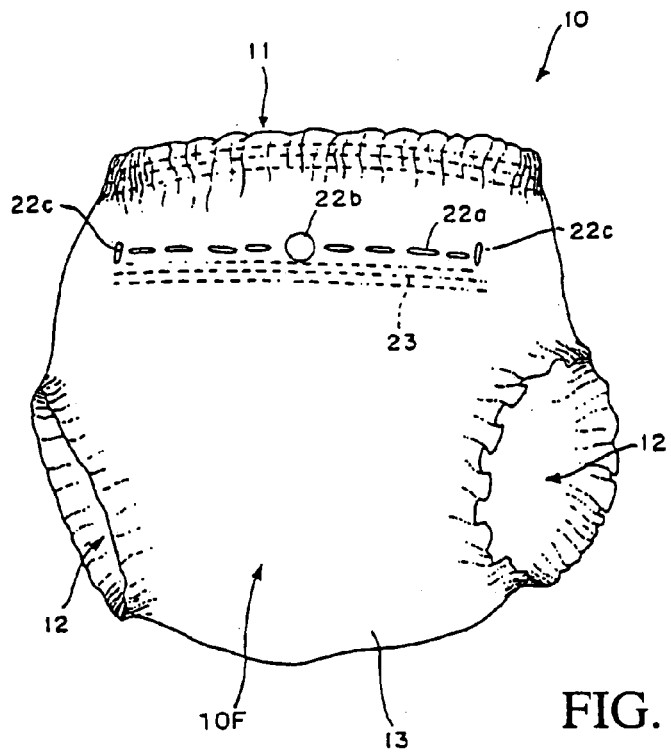
FIG. 9 is a perspective view which shows the appearance of another example of an absorptive product of the present invention.

In FIG. 9, elements which have the same function as those shown in FIG. 8 are shown by the same label and the repetitive description has been omitted. In FIG. 9, the front region 10F of the absorptive product 10 has a perforation line 22a which extends from the edge of the opening around the waist 11 in a slightly descending sideways direction, and this perforation line 22a has a finger hole 22b to make it easy to tear the perforation line 22a. Furthermore, a pair of end holes 22c are formed at the ends on the perforation line 22a in order to prevent tearing from continuing outward past either end of the perforation line 22a when the back sheet 13 is torn along the perforation line 22a. The end holes 22c in this example are preferably slit-shaped openings extending in a direction perpendicular to the direction of the perforation line 22a, but circular holes are also acceptable.

In this example, as long as the perforation line is not torn, the front access port 22 will not open. In other words, in this condition, because the front access port 22 is closed, there will not be a problem with the front access port 22 opening, which may cause difficulty in pulling up the crotch region when putting on the absorptive product 10. Later, when it is necessary to remove or insert the front absorber 21, fingers are inserted into the finger holes 22b and the back sheet 13 is pulled in order to tear the back sheet 13 along the perforation line 22a thus creating a front access port port 22 reaching to the end holes 22c on both sides.

In order to create a front access port 22 which can be opened and closed as necessary, a technician in this field could likely think of several alternate means besides those means mentioned above. For instance, it would also be possible to make a front access port 22 which could be opened or closed by means which use such methods as surface fasteners or adhesive tape. If a means to open and close the access port is set, it is possible to prevent the removable absorber from shifting and sticking out of the access port while in use.

Figure 10:
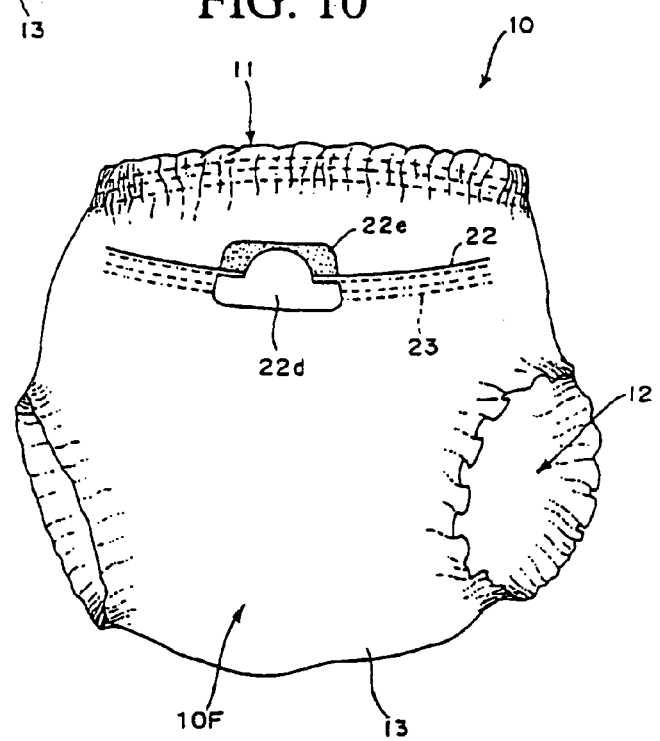
FIG. 10 is a perspective view which shows the appearance of an additional example of an absorptive product of the present invention.

For instance, it is possible to use an opening and closing means on the front region 10F of the absorptive product, which opening and closing means has mounted a pair of surface fasteners 22d, 22e which hold the front access port 22 as in FIG. 10 which shows the appearance of another example of the absorptive product of the present invention. In this example, one of the surface fasteners 22d is temporarily connected to the other surface fastener 22e, but when necessary, the access port can be opened by pulling on the surface fastener 22e. On the other hand, by over laying and attaching a surface fastener 22d to the other surface fastener 22e, the front access port 22 can be closed. As opening and closing means, it is possible to use methods such as snaps, buttons, or zippers as well as the above-mentioned surface fasteners 22d, 22e or adhesive tape.

With the absorptive product 10 of this embodiment, when feces are excreted, the feces are passed through the feces separator opening 17 in the top sheet 16 and are kept on the back sheet 13, so that after the absorptive product 10 has been removed from the wearer and only the feces are disposed of, and this absorptive product can be washed and reused.

Figure 11:
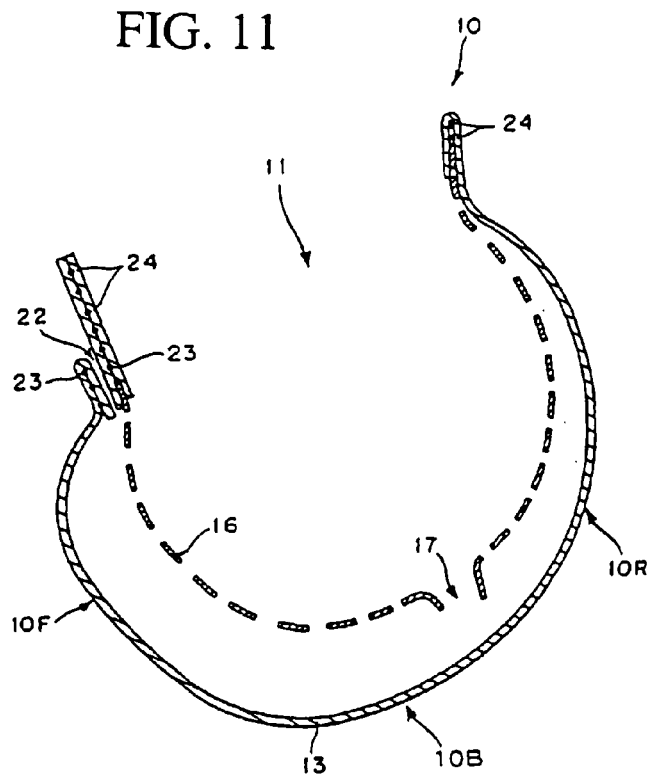
FIG. 11 is a cross section view on the line which runs from the front region through the crotch region to the rear region of the absorptive product shown in FIG. 10.

A cross section of another example of the absorptive product of the present invention is shown in FIG. 11 with the front absorber and rear absorber omitted. In this example, cloth which has been moisture-resistant treated on the inner surface, or water resistant humidity permeable materials like GORE-TEX are used for the back sheet 13 of the absorptive product 10, and it is acceptable to make the absorptive product 10 without the fixed absorber 14 shown in the example of FIG. 7, leaving only the front absorber 21 to absorb the urine.

In this example, net-like filament cloth is used for the top sheet 16, and the top sheet is made so that the permeability of urine is unhindered. Both lengthwise sides of said top sheet 16 are secured to the opening around the waist 11 by the back sheet 13. Said opening around the waist 11 contains an elastic member around the waist 24, and an access port 22 is set in the front region 10F of the absorptive product 10, and the points where the elastic member 23 are placed along said access port 22 are similar to the example shown in FIG. 5.

Figure 12:
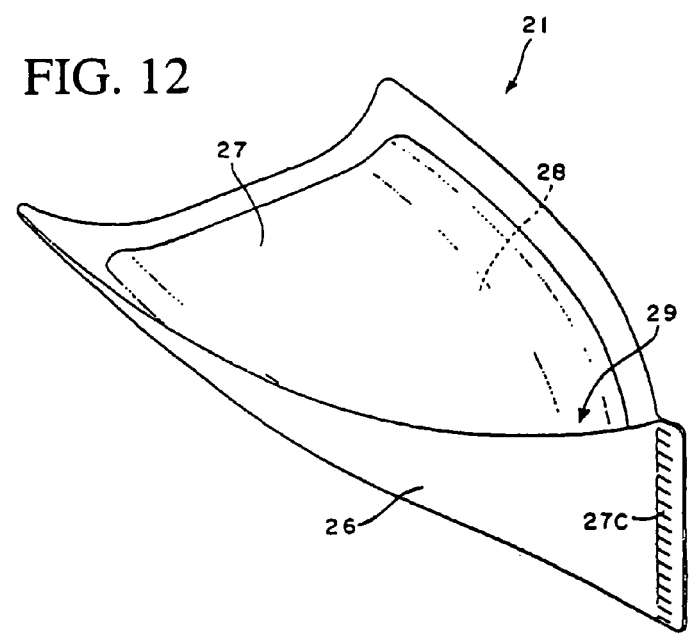
FIG. 12 is a perspective view which shows the appearance of an example of a removable absorber which is assembled into the absorptive products shown in FIGS. 5 through 11.
Figure 13:
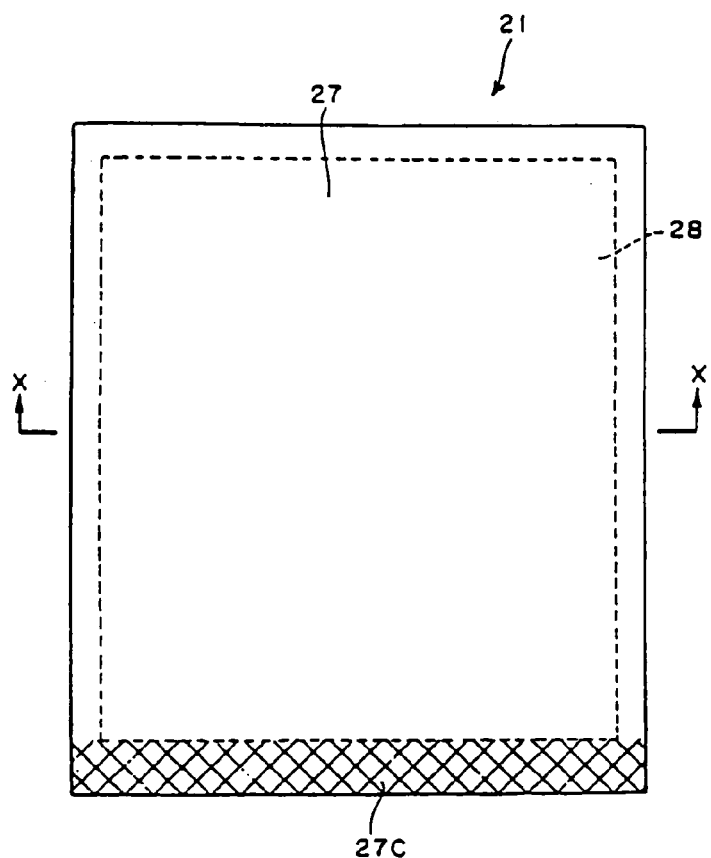
FIG. 13 is a plan view of the removable absorber shown in FIG. 12, shown here in an opened condition.
Figure 14:
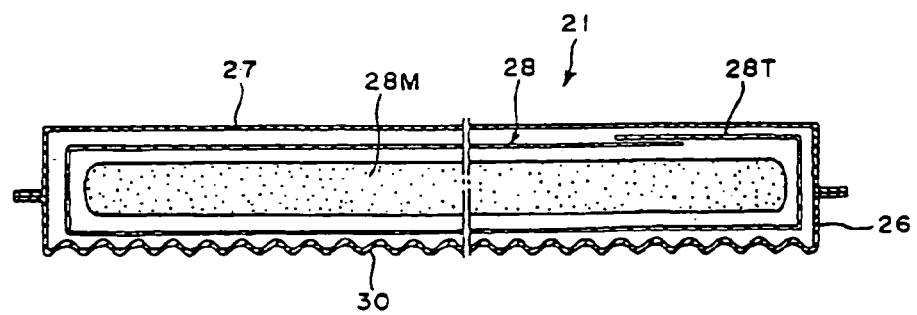
FIG. 14 is a cross section view along the line X—X in FIG. 13.
Figure 15:
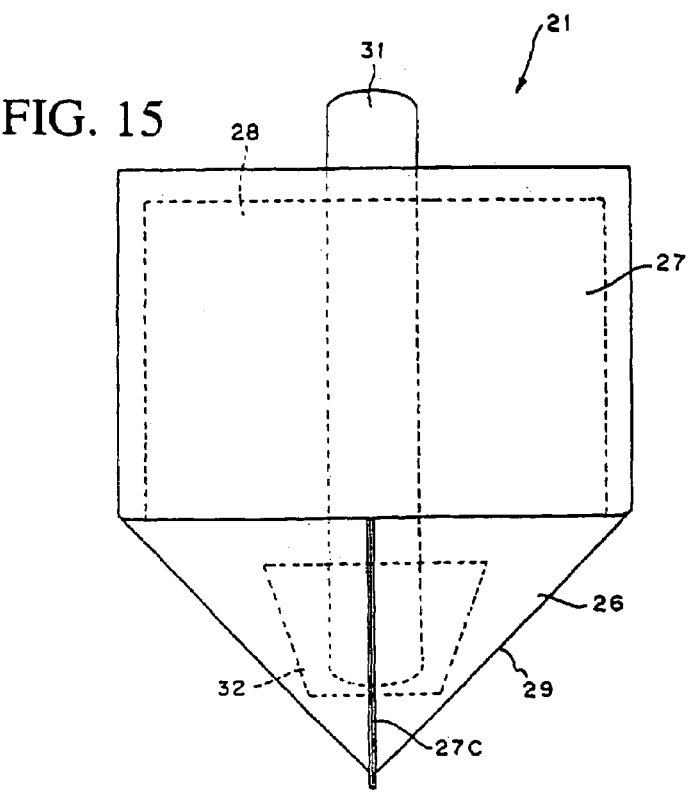
FIG. 15 is a plan view of the removable absorber shown in FIG. 12 which is attached to an applicator.

The appearance of the front absorber 21 for absorbing urine which is preferably applied to the absorptive product of the present invention shown in FIGS. 5 through 11 is shown in FIG. 12, the opened condition of said front absorber is shown in FIG. 13, the cross section along the X—X line shown in FIG. 13 is shown in FIG. 14, and the top view configuration is shown in FIG. 15.

In the present invention, the front absorber 21 is comprised of a liquid impermeable sheet 26 which is positioned on the side opposite the cover sheet 15, a liquid permeable sheet 27 which faces the top sheet 16 side, and an absorbent body 28 which is held in a condition sandwiched between the liquid impermeable sheet 26 and the liquid permeable sheet 27, and a receiving area 29 is formed to temporarily receive urine in case a large amount of urine is excreted. The receiving area 29 in this example is formed by taking the rectangular liquid permeable sheet in the opened condition and folding the joining area 27C (shown by the thatched area in FIG. 13) on one side of the liquid permeable sheet 27 in half, and fastening while overlaid.

The absorbent body 28 in this example is constructed by wrapping with tissue 28T a mixture mat 28M made by a mixing a material whose main component is fluff pulp made of fibrous wood pulp and non-wood pulp with a super-absorbent resin, and this construction is such that the super-absorbent resin is prevented from leaving the mixture mat 28 by said tissue 28T. Another possible alternative is to use a super-absorbent resin alone, or to use a mixture material or multi-layer material such as thermal fused fiber in place of above-mentioned mixture mat 28M. The absorbent body 28 is made by directly coating the liquid impermeable sheet 26 or the liquid permeable sheet 27 with a coating made by dispersing a super-absorbent resin and microfibril cellulose in a solution of water and propylene glycol or methanol, or by coating a non-woven material made of synthetic fiber whose primary ingredients are thermoplastic resin such as polyethylene, polypropylene, or polyester, and the absorbent body may be bonded to the liquid impermeable sheet 26 or to the liquid permeable sheet 27.

The front absorber of the absorptive product of the present invention is made by applying a treatment of a Super-Absorbent Polymer (hereafter referred to as SAP) to a material whose primary component is fluff pulp made of fibrous wood pulp or non-wood pulp, and other mixture materials or multi-layer materials like absorbent paper or thermal fused fiber may be preferentially used. Furthermore, it is also acceptable to make a multi-layer construction by wrapping the whole absorbent body with tissue in order to prevent the SAP from escaping. Specifically, either the top sheet is directly coated with a coating made by dispersing SAP or microfibril cellulose in a mixed solution of water and propylene glycol or methanol, or a sheet is made whose primary ingredient is the SAP which is coated on the non-woven material made of synthetic fibers whose raw materials are thermoplastic resins like polyethylene, polypropylene, or polyester.

For the front absorber, it is possible to use a liquid permeable material for the back sheet if a liquid impermeable sheet is attached to the back sheet to form a multi-layer construction, and thereby improve air permeability and prevent stuffiness.

Also, it is possible to attach adhesive tape or surface fasteners to the surface where the front absorber contacts the back sheet in order to make a construction where the front absorber can be removed or inserted but can be secured to the back sheet.

In this example, the liquid impermeable sheet 26 is made to have a drape area 30 which functions as a means for expansion in order to allow for volumetric expansion of the mixture mat 28M which accompanies the absorption of urine, but it is also acceptable to make said liquid impermeable sheet 26 capable of expansion by using the spun-lace method.

The liquid impermeable sheet 26 used for the front absorber 21 may be made of film or non-woven material whose raw material is common thermoplastic resins like polyethylene and polypropylene, but not much consideration for strength is required because it is double protected by the existence of the back sheet 13 on the outside, so it is sufficient to use a low-cost thinner material. Depending on the circumstances, it may also be omitted.

The liquid permeable sheet 27 used for the front absorber 21 may be made using a liquid permeable non-woven material made of synthetic fiber raw material of thermoplastic resin like a polyethylene, polypropylene, or polyester, similar to the top sheet. In particular, if a wet non-woven material made of pulp or rayon and the previously mentioned synthetic fibers are used, it will be able to be hydrolyzed, and may be flushed down the toilet.

The previously mentioned microfibril cellulose is an extremely minute fiber with an average fiber length below 0.1 mm, and is obtained by refining wood pulp under a high-speed shear. Also, the above-mentioned super-absorbent resin may be a starch, a cellulose or a synthetic polymer such as starch acrylate graft copolymer, starch ethyl acrylate graft copolymer saponification compounds, starch acrylnitrile graft copolymer saponification compounds, starch acrylamide graft copolymer saponification compounds, polyethylene oxide cross linked with acrylate polymers, or cross linked compounds of sodium carboxy-methyl cellulose, cross-linked compounds of the products of reacting polyvinyl alcohol anhydrous maleate, or cross linked compounds of polyasparate. In particular, poly-sodium acrylate compounds are preferable and can absorb over 20 times their weight in liquids like urine.

Also, in order to have a construction such that the applicator 31 can be used to simplify the operation of inserting or removing the front absorber when a used front absorber 21 is removed through the access port 22 and a new front absorber inserted while the absorptive product is being worn, the receiving area 29 of the liquid impermeable sheet 26 is connected to an insertion part 32 where the tip of the applicator is inserted.

The applicator 31 is to assist in inserting the front absorber 21 through the front access port 22 while the absorptive product 10 is being worn. In this example, it is a separate component from the front absorber 21 so the absorbency of the applicator is not an issue.

In contrast, the front absorber 21 must be capable of rapidly absorbing urine, so it is required to have dispersion properties. From this perspective, it is possible to use an applicator 31 with absorbent properties in order to facilitate dispersion, and in this case, it is possible for the applicator 31 to be combined with the front absorber 21. If the applicator 31 is not made to have this type of absorbent properties, it is also possible to have the applicator 31 separated from the front absorber 21.

Furthermore, it is also possible to give the applicator 31 a urine indicator function. For instance, if the end of the applicator 31 is made to be normally visible from the outside, and the applicator 31 is made so that this area has a visible indicator such as a color change when urine is absorbed up to the end of the applicator 31, then the applicator can be used as an indicator.

When the applicator 31 is made of a portion of the absorbent material, a portion of the absorbent material will function as the applicator so there is no need to make a separate applicator and costs can be reduced.

It is not necessary to use the fixed absorber 14 on the back sheet 13, but it is preferable to have a fixed absorber 14 on the back sheet 13 as in this example as a backup countermeasure in case urine is leaked from the front absorber 21, or to remove any water content included in the feces. This fixed absorber 14 may use the same material as the absorbent body 28 of the front absorber 21, but because it is not required to absorb large amounts of liquid, it can be made thinner. In some cases, it is possible to thinly coat the back sheet with a SAP so that it can function as both a fixed absorber and a back sheet.

Figure 16:
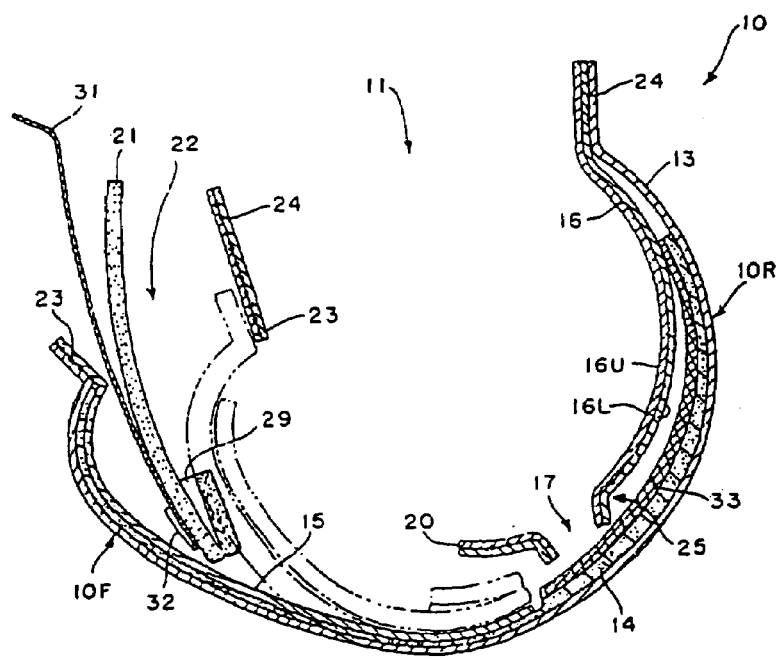
FIG. 16 is an lengthwise cross section view which shows the condition of the removable absorber when inserted using the applicator shown in FIG. 15 for another example of the absorptive product of the present invention.

The process of inserting a front absorber 21 using the applicator 31 shown in FIG. 15 is shown in FIG. 16. The front absorber is made so that the portion of the fixed absorber 14 which extends from the crotch region 10B to the rear region 10R is thicker than the portion in the front region 10F, and on top of that, a net layer 33 is fastened so that the movement of low viscosity soft stools can be effectively controlled.

As previously mentioned, the front absorber 21 is primarily for absorbing urine so it is preferable to fold up the absorbent body 28 to create a bellows or multi-layer construction so that the amount of liquid absorption per unit area or unit volume can be increased. Furthermore, it is desirable to include an acquisition layer for the receiving area 29, or a dispersion sheet which can quickly disperse the urine so that the urine can be temporarily held until it is absorbed by the absorbent body 28. Preferred materials for the acquisition layer are bulky non-woven materials like synthetic fiber whose raw materials are thermoplastic resins like polyethylene, polypropylene, or polyester. Said acquisition layer disperses the urine to the absorbent body 28, and acts to retain the urine at the front absorber 21 until it can be absorbed by the strong hydrophilic resin. Therefore, the urine can be rapidly absorbed from the liquid permeable sheet by the absorbent body 28. The dispersion sheet is preferably a pulp sheet made of wood pulp or non-wood pulp, and fabricated using wet paper processing or dry processing methods. Said dispersion sheet uses the capillary action of the pulp fiber to disperse the absorbed urine in a planar direction.

Figure 17:
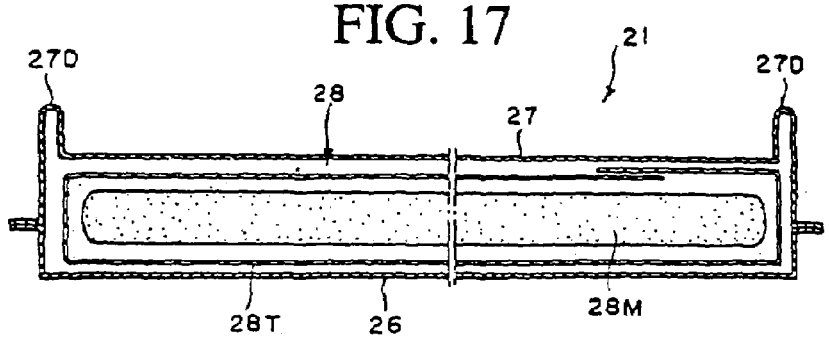
FIG. 17 is a cross section view which shows another example of the removable absorber of the present invention.

In the previously mentioned example, the liquid impermeable sheet 26 was made with a drape area 30 in order to allow for volumetric expansion of the mixture mat 28M that accompanies the absorption of urine, but it is also possible to provide an expansion means for the liquid permeable sheet 27. In the cross section of an additional example of the front absorber 21 shown in FIG. 17, a pair of overlaps 27D which can increase in width are established as an expansion means in the region around the area where the liquid permeable sheet 27 is connected to the liquid impermeable sheet 26, and these overlaps 27D will open up with the volumetric expansion of the mixture mat 28M associated with the absorption of urine.

Figure 18:
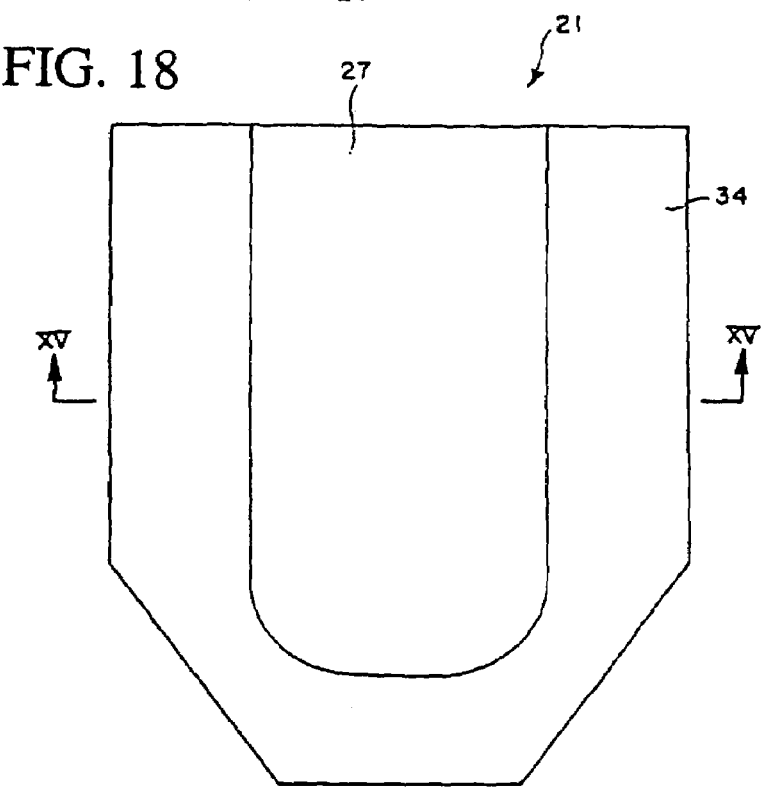
FIG. 18 is a plan view of another example of the removable absorber of the present invention.
Figure 19:
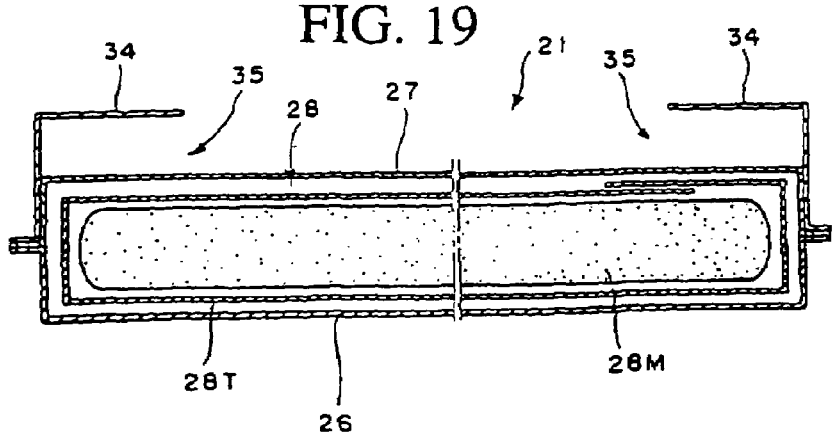
FIG. 19 is a cross section view along the line XV—XV in FIG. 18.

The top view configuration of another example of the front absorber 21 for the absorptive product of the present invention is shown in FIG. 18, and the cross section at line XV—XV is shown in FIG. 19. In this example, the front absorber 21 has a liquid impermeable pocket sheet 34 fastened along the side and bottom edges to the liquid permeable sheet 27, and a dam 35 rising from the surface of the liquid permeable sheet 27 is made in a U-shape. By forming this dam 35, urine is prevented from flowing from the front absorber 21 along the back sheet 13 side and mixing with the feces for the time the urine is passing through the liquid permeable sheet 27 until it is absorbed by absorbent body 28.

Figure 20:
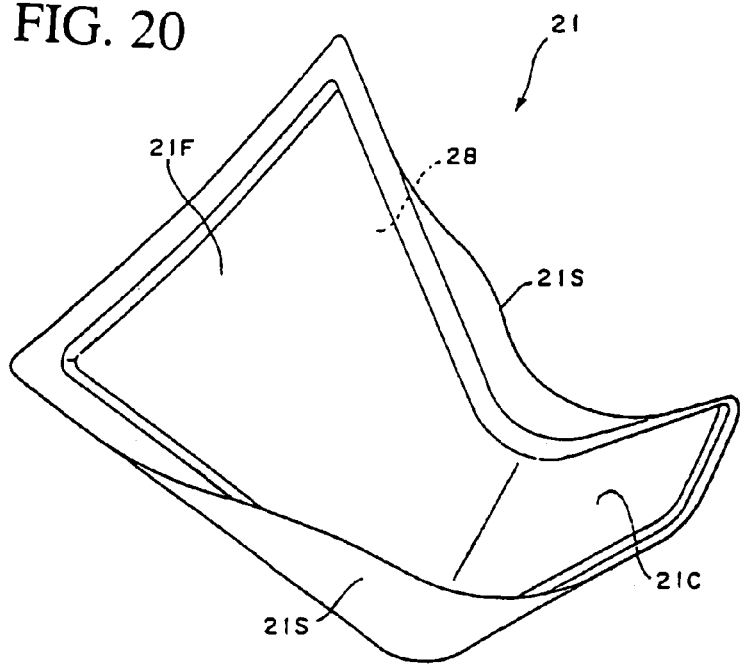
FIG. 20 is a perspective view which shows the appearance of an additional example of the removable absorber of the present invention.
Figure 21:
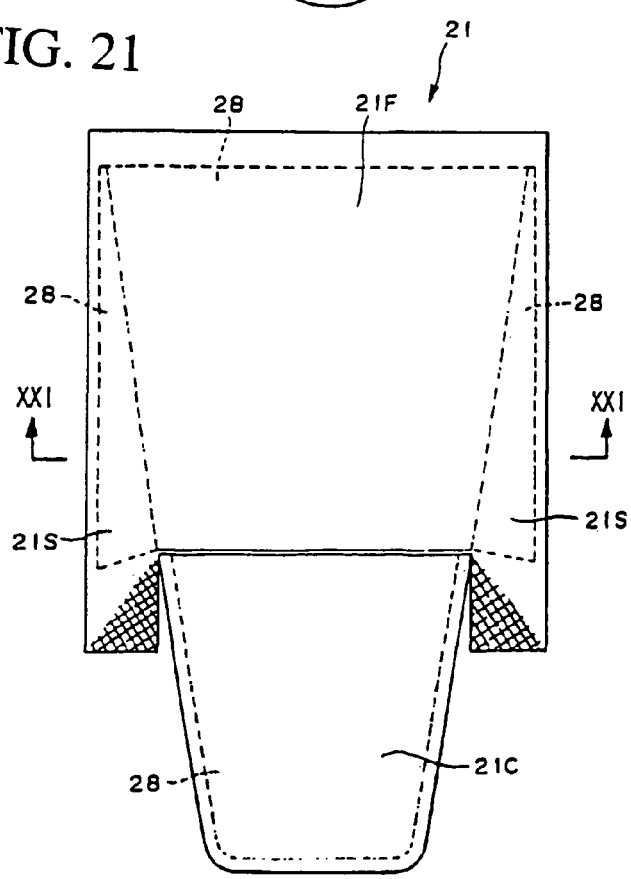
FIG. 21 is a plan view of the removable absorber shown in FIG. 20, shown here in an opened condition.
Figure 22:
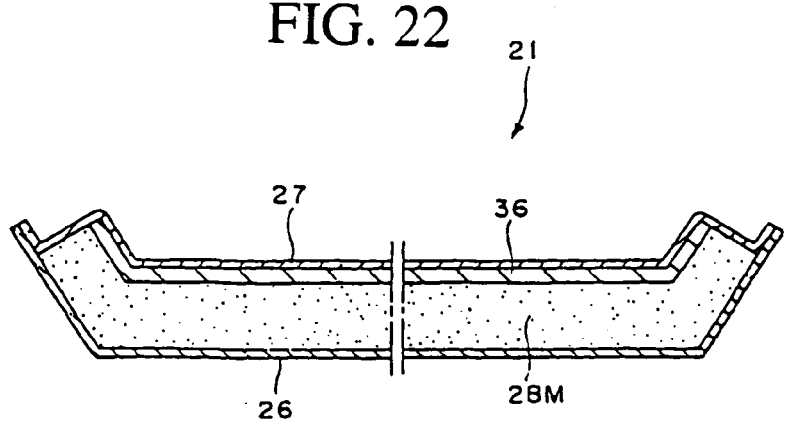
FIG. 22 is a cross section view of the removable absorber shown in FIG. 20 along the line XXI—XXI shown in FIG. 21.

FIG. 20 through FIG. 22 show the front absorber applicable to further examples of the absorptive product of the present invention. FIG. 20 shows the appearance of the front absorber, FIG. 21 shows the opened configuration, and FIG. 22 shows the cross section along the line XXI—XXI of FIG. 21. In these drawings, elements which have a function similar to those shown in the previous example are referred to by the same flag, and detailed descriptions of those have been omitted.

As can be clearly seen from FIG. 21, the front absorber 21 in this example has a front portion 21F, a crotch portion 21C, and sides on the left and right 21S, and the thatched regions shown in FIG. 21, or in other words, the ends of the sides 21S, are connected to the crotch portion 21C, thus forming a three dimensional construction which extends downward, which causes the sides 21S to function as the previously mentioned dam. Furthermore, an acquisition layer 36 is formed on the mixture mat 28M so that when coupled with existing previously mentioned sides 21S, urine can be prevented from leaking out of the front absorber 21.

Figure 23:
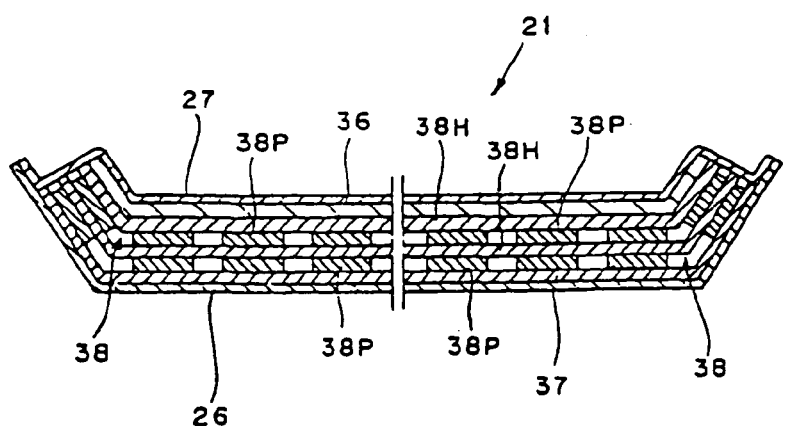
FIG. 23 is a cross section view of an additional example of the removable absorber of the present invention.
Figure 24:
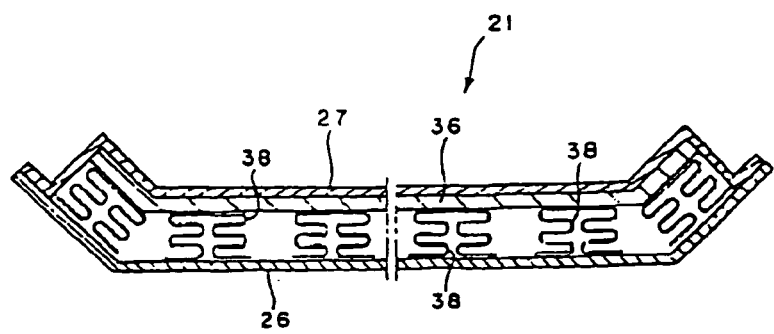
FIG. 24 is a cross section view of yet another example of the removable absorber of the present invention.

The absorbent body 28, which is the major component of the front absorber 21, may use other suitable constructions in addition to the previously mentioned example like those shown in FIG. 23 and FIG. 24.

The absorbent body 28 shown in FIG. 23 is made by placing between the liquid impermeable sheet 26 and the liquid permeable sheet 27, multiple layers in the following order: a dispersion sheet 37, two SAP sheets made by applying alternating strips of microfibril cellulose and superabsorbent resin onto a hydrophilic sheet 38H to make a coated laminate 38P, and an acquisition layer.

Furthermore, in the additional example shown in FIG. 24, the absorbent body 28 is constructed with several layers of SAP folded over in a bellows configuration, covered by an acquisition layer 36 and assembled between the liquid impermeable sheet 26 and the liquid permeable sheet 27.

In the preferred embodiments described while referring to FIGS. 8 through 24, the front absorber, as the component to handle urine, is positioned interiorly of the back sheet in the front region 10F, and is made to be able to be removed or inserted through the access port established in the front region. Besides these forms, the present invention also provides an absorptive product which has a rear absorber for handling feces.

Figure 25:
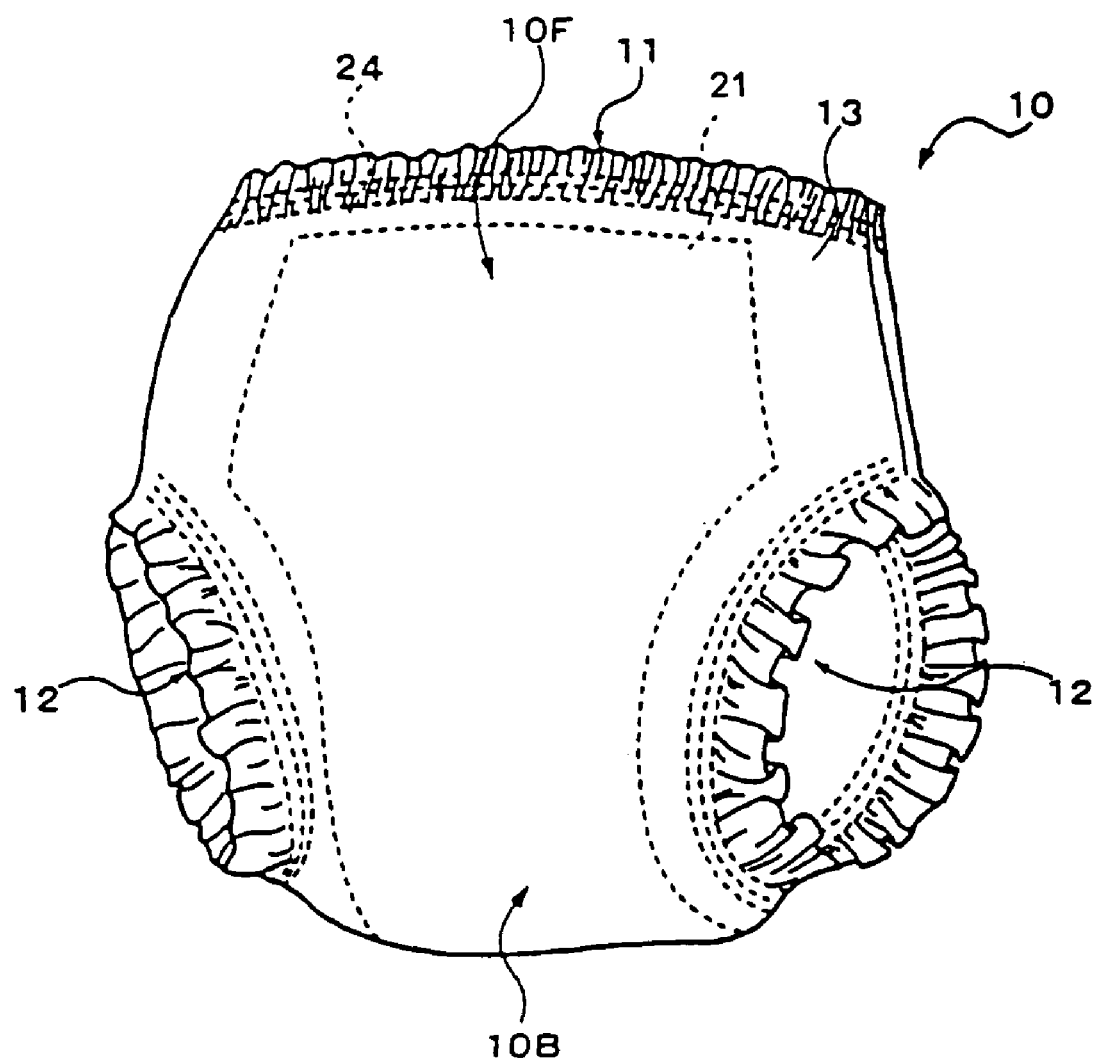
FIG. 25 is a perspective view which shows the appearance of one embodiment where the absorptive product of the present invention is applied to a diaper.
Figure 26:
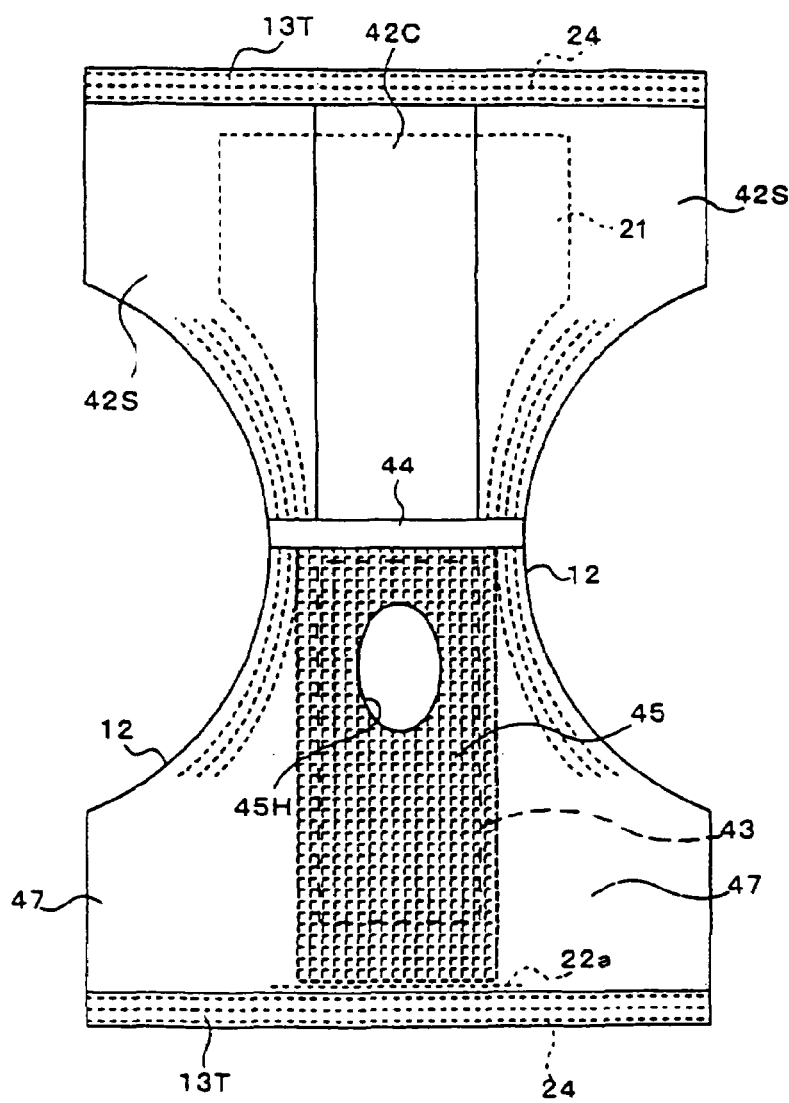
FIG. 26 is a plan view of the absorptive product shown in FIG. 25, showing the interior in an open condition.
Figure 27:
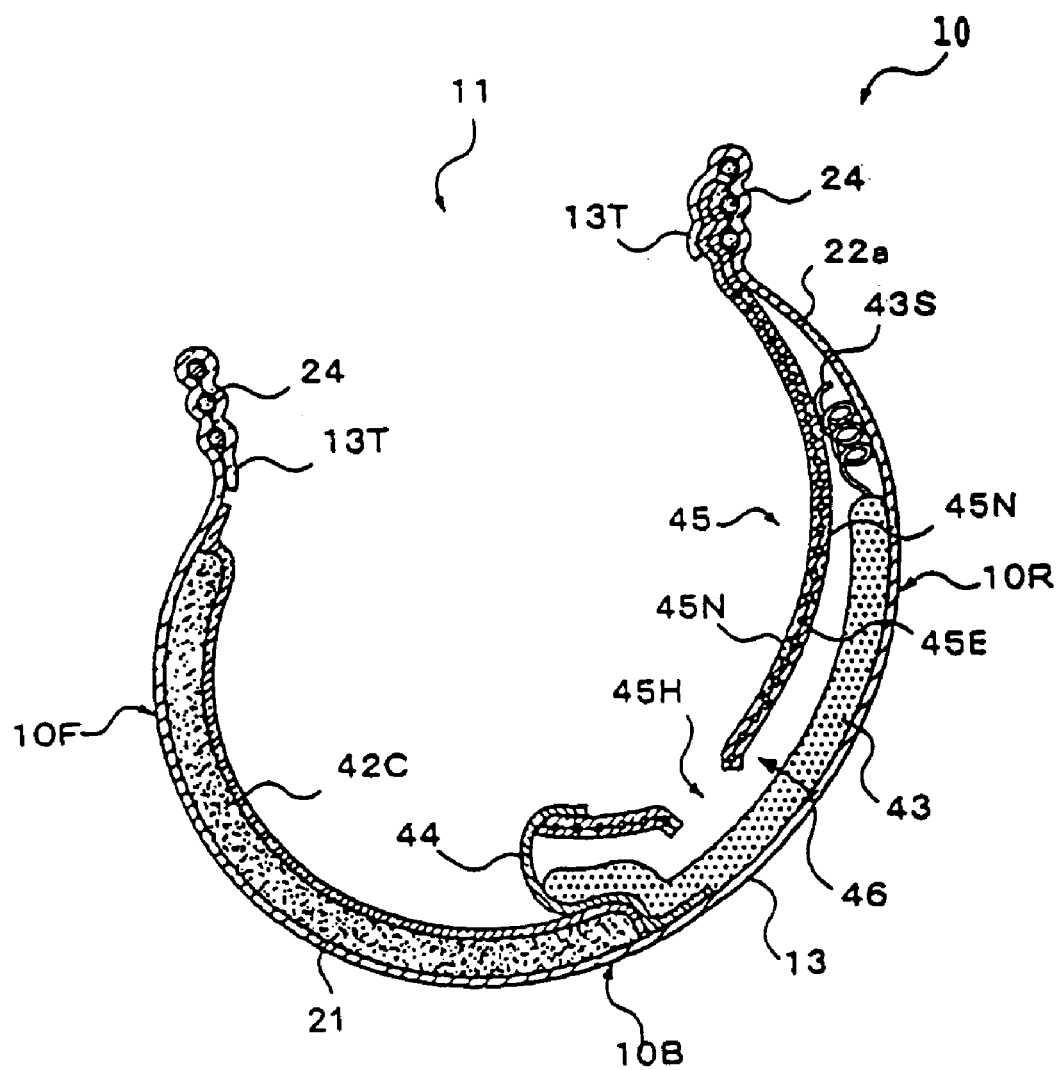
FIG. 27 is a cross section view lengthwise along the center of the absorptive product shown in FIG. 25.

The absorptive product based on the preferred embodiment of the present invention which has a rear absorber for handling feces is shown in FIG. 25 through FIG. 27. The absorbent product 10 shown in the drawings is similar to the previously mentioned absorptive product of the present invention, and is in a pants form with a front region 10F, a rear region 10R, and a crotch region 10B, and has a liquid impermeable back sheet 13 which is formed with one opening around the waist 11 and a pair of openings around the legs 12. The back sheet 13 is made with a fold-over 13T which is folded toward the inside at an appropriate width on the edge which makes the edge of the opening around the waist 11, and an elastic member around the waist 24 is retained inside of said fold-over 13T.

As shown in FIG. 26 and FIG. 27, interiorly of the back sheet 13 are placed a urine absorbing front absorber 21 which extends from the front region 10F to the crotch region 10B, and a rear absorber 43 which extends from the crotch region 10B to the rear region 10R.

As will be described in detail later, in the example of FIG. 26 and FIG. 27, the front absorber 21 is secured to the back sheet 13, but the rear absorber 43 is not secured to the absorptive product. Furthermore, a perforation line 22a is made in the back sheet 13 in a location slightly higher than the top edge of the rear absorber 43. Similar to the example shown in FIG. 9, this perforation line is made so that the back sheet 13 can be torn to create an opening, or in other words, a rear access port.

As shown in FIG. 26 and FIG. 27, side top sheets 42S positioned on both sides and a center top sheet 42C cover the front absorber 21 interiorly of the back sheet 13.

A partition 44 extends from edge to edge of the openings around the legs 12 of the crotch region 10B of the absorptive product 10, and is mounted between the front absorber 21 and the rear absorber 43 in order to prevent contact between the two absorbers.

Flag 45 refers to a feces separator sheet which is made of a nearly rectangular liquid impermeable sheet-like material capable of expansion, and which is made with a feces separator opening 45H at the appropriate position of its crotch portion. This feces separator sheet 45 extends from the crotch portion 10B to the top edge of the rear region 10R, and the upper end is secured between the back sheet 13 and the fold-over 13T, and the lower end is secured to the partition 44. A void is created between this feces separator sheet 45 and the rear absorber 43 at least in the area of the feces separator opening 45H. Flag 47 depicts a left and right pair of assist sheets which are placed to cover the inside of the back sheet 13 so that the inside edges overlap both of the widthwise side edges of the feces separator sheet 45.

The partition 44 is connected on one lengthwise side to the back sheet in the crotch region, and the other sides are connected to the top sheet or the feces separator sheet. Although not shown in the drawing, another acceptable option is to use two partitions, and connect one of the lengthwise sides of both partitions to the back sheet, and connect the other side of one to the top sheet and the other side of the other one to the feces separator sheet in order to more positively separate the feces and urine. Films and non-woven materials whose raw materials are thermoplastic resins like polyethylene, polypropylene, or polyester may be used for the partitions. If a non-woven material is to be used, a construction using spun bond (S) and melt blown (M) in a complex SMS or SMMS configuration is preferable.

Also, for the absorptive product of the present invention, if all of the components other than at least one removable absorber in the front or the back are made of cloth and the main component of the absorptive product is made by sewing, then it will be possible to dispose of the removable absorber only, and to wash and reuse the main component when it becomes soiled.

The rear absorber for the absorptive product of the present invention can use a hydrolyzable paper sheet which uses rayon, pulp, or CMC-Ca as the top layer, can use fluff pulp or curly fiber as the absorbent core, and can use a water resistant sheet made of tissue laminated with PVA for the back layer. In this case, it is preferable for the absorbent core to use as the main material fluff pulp made of fibrous wood pulp or non-wood pulp treated with SAP. By keeping the SAP at less than 10 wt %, the rear absorber can maintain its hydrolyzable properties.

Figure 28:
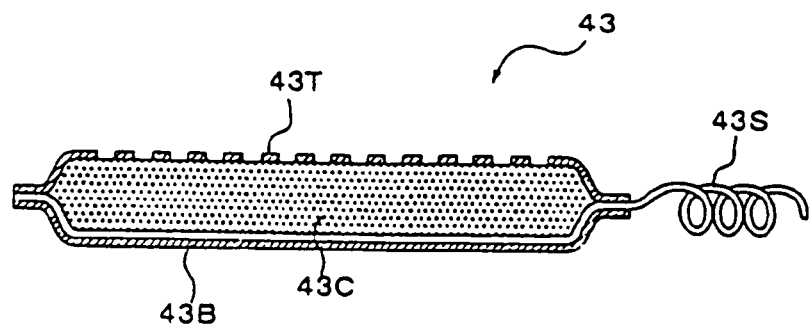
FIG. 28 is a cross section view showing the rear absorber in the removed condition for the preferred embodiment shown in FIG. 27.

As shown in FIG. 28, the rear absorber 43 of this preferred embodiment has an absorbent core 43C, which uses curly fiber, held between a hydrolyzable top layer 43T which may be rayon or pulp for example, and a water resistant back layer 43B made by laminating tissue with PVA, and one side has a string 43S attached as a handle. This string 43S is provided so that, after creating the opening or access port by tearing along the perforation line 22a, the rear absorber 43 can be removed without getting the hands dirty by grasping and pulling on one end of the string. In place of the string 43S, it is also possible to use tape or ribbon.

Figure 29:
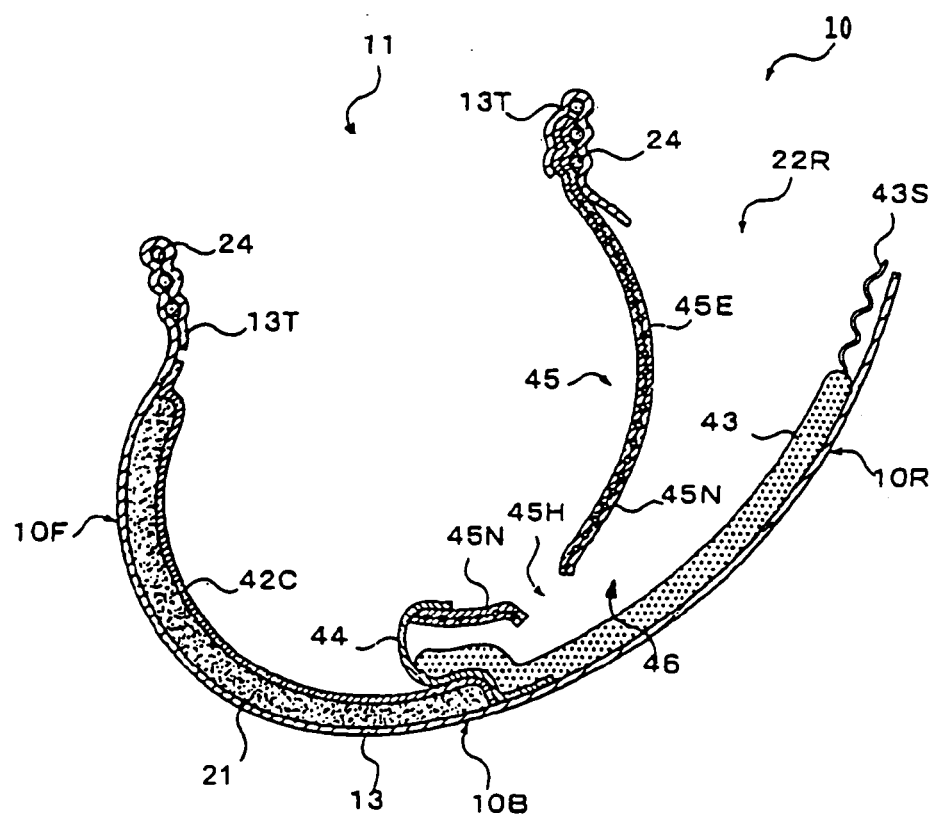
FIG. 29 is a cross section view of an exemplary absorptive product including the rear absorber shown in FIG. 27 and FIG. 28.

As shown in FIG. 29, the feces separator sheet 45 of this preferred embodiment, which is made with a feces separator opening 45H in the crotch region 10B for the feces to pass through, is preferably made by sandwiching an elastic net 45E between two sheets of non-woven material 45N in an elongated condition. In this example, the feces separator sheet 45 is connected on one side to the edge of the partition 44, and is connected in a condition held between the back sheet 13 fold-over 13T at the edge of the opening around the waist 11. It is preferable that the length dimension of the feces separator sheet 45 be set shorter than the dimension of the rear region 10R in the opened condition when the tensile force is relieved. Under these conditions, the feces separator sheet 45 will be suspended from the back sheet 13, and a void 46 will be created between the feces separator sheet 45 and the rear absorber 43. Because of the existence of the void 46, the feces will pass through the feces separator opening 45H, move to the outside of the feces separator sheet 45, and be retained by the rear absorber 43, so that the feces will not directly contact the buttocks.

FIG. 29 shows the condition where part of the back sheet 13 has been torn along the perforation line 22a and the opening or rear access port 22R has been opened wide so that the rear absorber 43 can be removed after excretion. In this condition, the whole rear absorber 43 can be pulled upward and can be pulled out through the rear access port 22R by grasping and pulling up on the connected string 43S. Later, if the absorptive product 10 is removed from the wearer, the wearer or the caregiver will not soil their hands by this operation.

The string 43S used as a handle for the rear absorber 43 in the present invention can be made from a commonly used hydrolyzable material such as paper or PVA film, or combinations of these, and rather than a string form, it is also acceptable to use a form like tape if it can easily pull out the absorber without soiling the hands of the caregiver.

In the preferred embodiment mentioned above, the top sheet is comprised of several components including the center top sheet 42C, a pair of left and right side top sheets 42S, and an assist sheet 47, but of course it is also possible to use individuals sheets of these materials.

Figure 30:
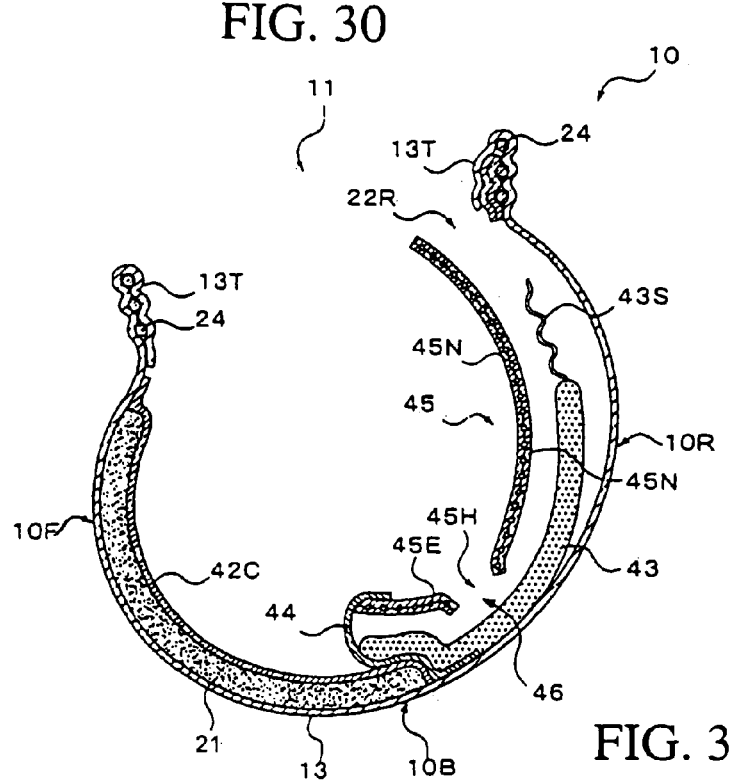
FIG. 30 is a cross section view of the absorptive product of FIG. 27 showing the rear absorber in a partially removed condition.

Furthermore, the rear access port 22R is formed in the back sheet 13, but as shown in FIG. 30, it may also be formed in the feces separator sheet 45. It is possible to have a construction such that even if the rear access port 22R is formed in the feces separator sheet 45, a perforation line is made in the appropriate location of the feces separator sheet 45, so that when it is necessary to remove the rear absorber 43, the feces separator sheet 45 is torn by using this perforation line to make the rear access port 22R.

With the present invention, it is advantageous to form the back sheet or the feces separator sheet with a rear access port for removing the rear absorber. The position of this rear access port may be freely selected in the region between the crotch region and the back region, and a specific form is not required as long as the removable absorber can be removed through the access port. For instance, it is acceptable to put a perforation line in the back sheet or feces separator sheet and this perforation line is torn to create the rear access port when the rear absorber is to be removed. Alternately, a recloseable opening equipped with adhesive tape, zipper, or surface fastener may be made beforehand for the access port, and this is also effective when considering that the access port will not be opened unintentionally. If a rear access port is not made, the rear absorber could be removed by using a construction such that the feces separator sheet can be separated from the back sheet.

The two examples shown in FIG. 24 through FIG. 30 may also have an appropriate temporary closure means to close the rear access port 22R, similar to the example shown in FIG. 10. If this type of closure means is used, the rear access port 22R may be closed again after a new rear absorber 43 has been inserted so that the other elements of the absorptive product may be reused again.

Figure 31:
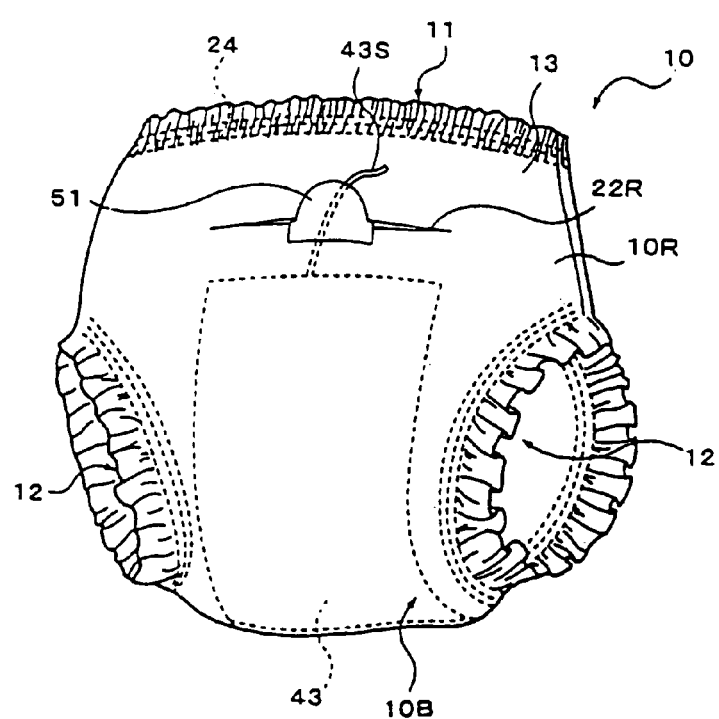
FIG. 31 is a perspective view which shows the appearance of the rear region for another preferred embodiment where the absorptive product of the present invention is applied to a diaper.
Figure 32:
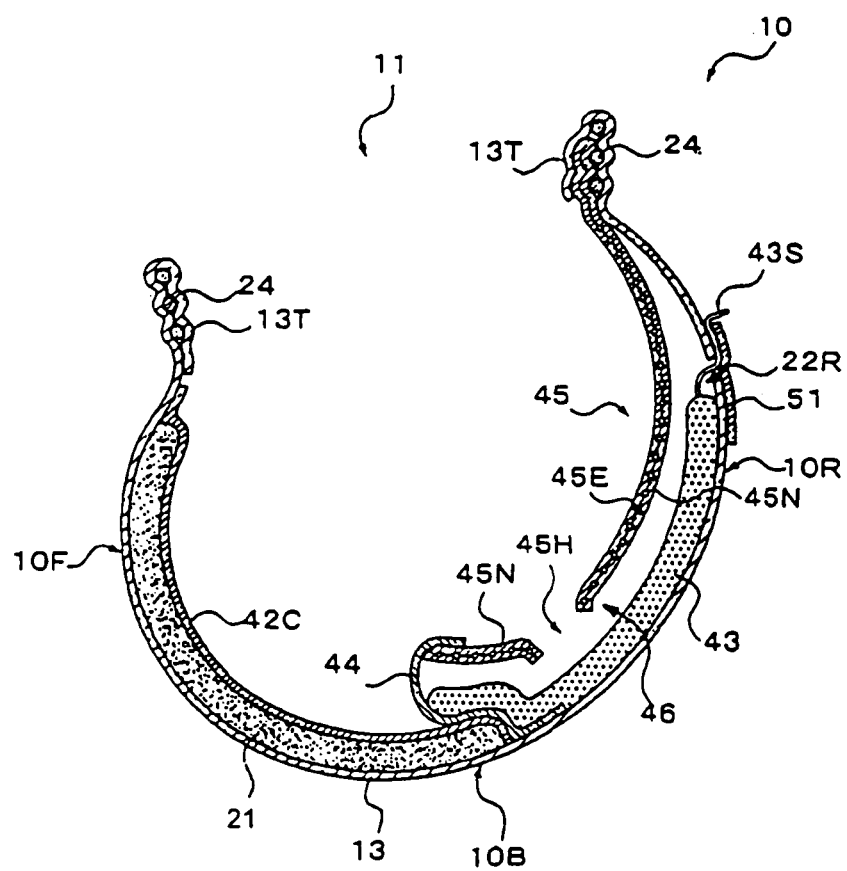
FIG. 32 is a cross section view lengthwise along the center of the absorptive product shown in FIG. 31.

An example of an absorptive product of the present invention with this type of construction is shown in FIG. 31 and FIG. 32. FIG. 31 shows the appearance as seen from the back side of the back sheet 13, and FIG. 32 shows the cross section condition at the center from the front region around to the back region. In FIG. 31 and FIG. 32, identical or equivalent elements are shown using the same flags as shown in the previous preferred embodiment, and the redundant descriptions have been omitted.

In FIG. 31 and FIG. 32, a slit in the rear region 10R of the absorptive product 10 is made which is positioned an appropriate distance from, and extends nearly parallel to, the edge of the opening around the waist 11, and this slit is used as a rear access port 22R. Adhesive resealable tape 51 to close this rear access port 22R is placed to connect the two opposing parts on either side of the rear access port 22R, and is attached to one of the parts, but for the other part, it has only enough adhesion so that it can be peeled off. The end of the string 43S of the rear absorber 43 is preferably sandwiched between the adhesive resealable tape 51 and the back sheet 13, and extends to the outside of the construction.

When it is necessary to remove the rear absorber 43, one end of the adhesive resealable tape 51 is peeled off of the surface of the back sheet 13, and then string 43S is peeled off of the adhesive resealable tape 51. By doing this, the rear access port 22R can be opened wide, and in this condition, by pulling on the string 43S, the rear absorber 43, which is connected to the string 43S, can easily be pulled out through the rear access port 22R without inserting hands or fingers interiorly of the back sheet 13.

Figure 33:
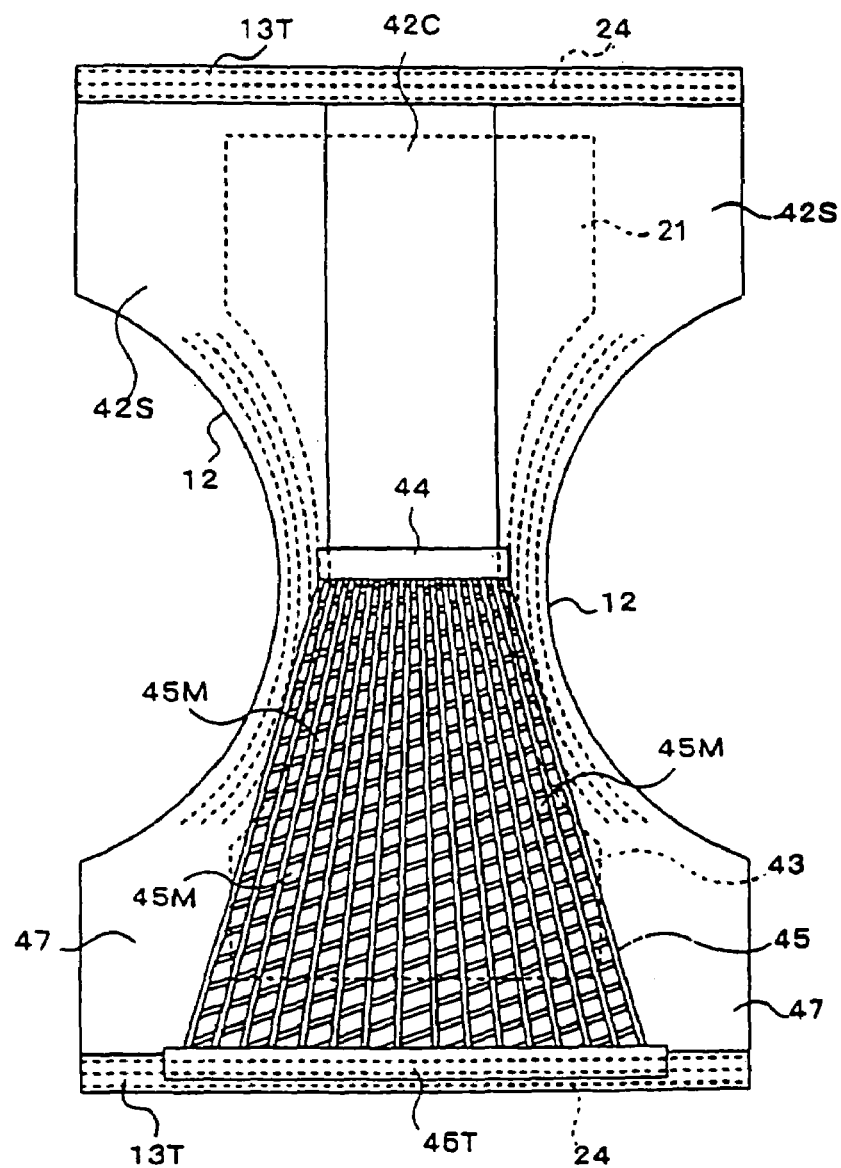
FIG. 33 is a plan view of the interior of another preferred embodiment in the opened condition, where the absorptive product of the present invention is applied to a diaper.

In the preferred embodiment shown in FIG. 25 through FIG. 32, there is a void 46 between the feces separator sheet 45 and the rear absorber 43, but if the feces separator sheet 45 is made of a foam resin material, that thickness can be utilized to obtain the same effect as if there was a void. For instance, in the example shown in FIG. 33, the feces separator sheet 45 is made of fibrous foam resin in a mesh configuration, and the edge of the opening around the waist 11 is connected to the fold-over 13T of the back sheet 13 by adhesive tape 45T.

With this type of feces separator sheet 45, the fibrous mesh 45M works as multiple openings for the feces to pass through even though there is no feces separator opening 45H. Furthermore, this mesh 45M forms a void, whose size is dependent on the thickness of the foam resin fibers, between the buttocks of the wearer and the rear absorber 43, and the feces are retained in this void.

In the example of FIG. 25 through FIG. 33, the front absorber 21, whose main purpose is to absorb urine, is secured to the back sheet 13, but of course it is possible to construct in a manner where the front absorber 21 can be removed from the absorptive product in the same manner as the rear absorber 43.

Figure 34:
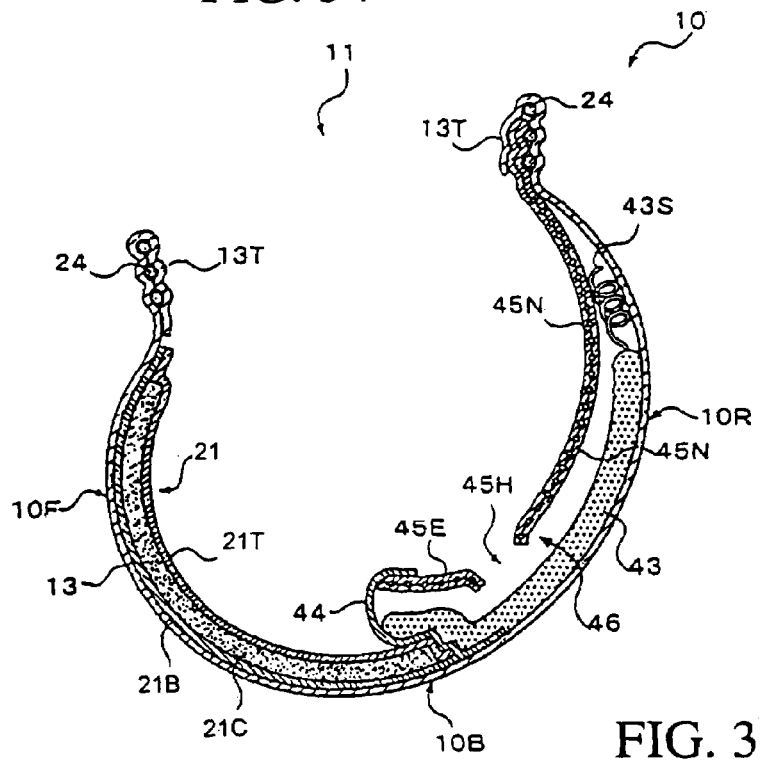
FIG. 34 is a cross section view lengthwise along the center of an additional preferred embodiment where the absorptive product of the present invention is applied to a diaper.

The lengthwise cross section across the middle of the absorptive product 10 of the present invention which has been constructed so that the front absorber 21 can be removed is shown in FIG. 34. In this example, the front absorber 21 is constructed with a top layer 21T, a back layer 21B, and an absorbent core 21A which is placed between the top layer 21T and the back layer 21B. The back layer 21B has adhesive properties with regard to the back sheet 13, and this adhesive force is used to hold the front absorber 21 onto the back sheet 13.

Figure 35:
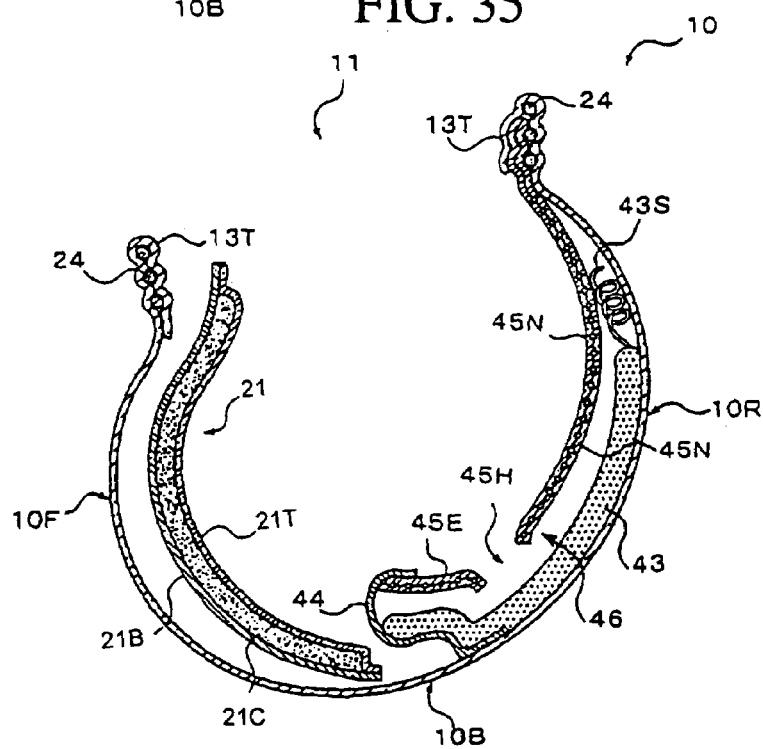
FIG. 35 is a cross section view lengthwise along the center showing the front absorber being removed from the absorptive product shown in FIG. 34.

The front absorber 21 can be removed from the back sheet 13 as shown in FIG. 35 by overcoming the adhesive force of the back layer 21B by pulling the front absorber 21 from the back sheet 13. In other words, the previously mentioned back layer 21B makes it possible to remove the front absorber 21, and if necessary, replace it with a new front absorber 21.

In this preferred embodiment, the front absorber 21 is not covered by a liquid permeable center top sheet 42C similar to the previous preferred embodiment, so that the front absorber 21 can be removed, but it is possible to make the top layer 21T of the front absorber 21 of the same material as the center top sheet 42C. If the back sheet 13 is made of a liquid impermeable material, it is not necessary to make the back layer 21B from a liquid impermeable material, and any material may be used. However, it is preferable that the back layer 21B be made of a liquid impermeable material so that the back sheet 13 can be made of a liquid permeable material, and stuffiness can be reduced. Furthermore, in the preferred embodiment of the present invention, the back sheet 13 covers as far as the fold-over 13T at the edge of the waist, but it would also be within the extent of the present invention to have an air permeable construction where the area covered by the back sheet ends in the area below the edge at the waist, and the fold-over is made of only the top sheet, so that there is no back sheet at the edge of the waist.

As can be understood from the above description, the fundamental effect of the absorptive product of the present invention is to separate the urine and feces, and to provide an opening or in other words, an access port for removing or handling and removing a removable absorber, thereby making it possible to remove only the removable absorber if either urine or feces are excreted, while leaving the absorptive product in place.

The absorptive product of the present invention can be used as a product to handle urine or feces in any form, and includes diapers for infants and caregivers, as well incontinence products for adults, and a pair of side banks established at an interval wherein said removable absorber can be stored.

What is claimed is:

1. An absorptive product having a front region, a rear region, and a crotch region and forming a waist opening and a pair of leg openings, comprising:
   a back sheet made of a liquid impermeable sheet;
   absorbers disposed interiorly of said back sheet and comprising a front absorber primarily for absorbing urine and extending from said front region to said crotch region and a rear absorber primarily for holding feces and extending from said crotch region to said rear region; and
   a partition disposed in the crotch region between said front absorber and said rear absorber such that contact between said front absorber and said rear absorber is prevented, said partition comprising a film, wherein at least one of said front absorber and said rear absorber is made to be removable from said absorptive product, and wherein said absorptive product has an access port for removing at least one of said front absorber and said rear absorber from said absorptive product while said absorptive product is being worn by a wearer.

2. An absorptive product as in claim 1 further comprising a fixed absorber extending from said front region to said rear region and a top sheet interiorly covering said front absorber and said fixed absorber, wherein said top sheet has a feces separator opening formed in an area of said absorptive product which corresponds to a feces excreting region of said wearer.

3. An absorptive product as in claim 1 further comprising a fixed absorber extending from said front region to said rear region and a top sheet interiorly covering said rear absorber, wherein said top sheet has a feces separator opening formed in an area of said absorptive product which corresponds to a feces excreting region of said wearer.

4. An absorptive product as in any one of claims 2 and 3 further comprising elastic members which are connected to said top sheet in an expanded condition and which surround said feces separator opening in said top sheet.

5. An absorptive product as in claim 2 or claim 3 further comprising an opening in said top sheet exposing a part of said front absorber which is located in said front region.

6. An absorptive product as in claim 2 or claim 3 wherein said top sheet is connected to said partition at said crotch region.

7. An absorptive product as in claim 1 further comprising a fixed absorber extending from said front region to said rear region and a feces separator sheet interiorly covering said rear absorber.

8. An absorptive product as in claim 1 further comprising a feces separator sheet interiorly covering said rear absorber.

9. An absorptive product as in claim 7 or claim 8 further comprising a top sheet interiorly covering one of said absorbers disposed in said front region.

10. An absorptive product as in claim 7 or claim 8 further comprising an opening in said feces separator sheet exposing a part of said rear absorber which is located in said rear region.

11. An absorptive product as in claim 7 or claim 8 wherein said feces separator sheet has a feces separator opening in an area of said absorptive product which corresponds to a feces excreting region of said wearer.

12. An absorptive product as in claim 8 wherein said feces separator sheet is connected to said partition at said crotch region.

13. An absorptive product as in claim 1 further comprising a feces separator sheet that is connected to said partition at said crotch region and to said back sheet at an edge of said waist opening and is not connected to other elements, such that a pocket-shaped void space is created between said feces separator sheet and one of said absorbers disposed in said rear region.

14. An absorptive product as in claim 1, claim 2, claim 3, claim 7, claim 8, or claim 13 wherein a position control means is provided to maintain said removable absorber in a designated location interiorly of said back sheet.

15. An absorptive product as in claim 14 wherein said position control means is formed by said partition and a pair of side banks disposed at an interval wherein said removable absorber can be stored in said interval between said side banks.

16. An absorptive product as in claim 14 wherein said position control means is a pocket-like trap into which a part of said removable absorber can be inserted.

17. An absorptive product as in claim 1, claim 2, claim 3, claim 7, claim 8, or claim 13 wherein said access port extends adjacent and generally parallel to an edge of said waist opening.

18. An absorptive product as in claim 1, claim 2, claim 3, claim 7, claim 8, or claim 13 further comprising an elastic member attached to said back sheet adjacent and generally parallel to said access port and providing a contractive force tending to keep said access port in a closed condition.

19. An absorptive product as in claim 1, claim 2, claim 3, claim 7, claim 8, or claim 13 further comprising an opening and closing means adapted for use in opening and closing said access port.

20. An absorptive product as in claim 1, claim 2, claim 3, claim 7, claim 8, or claim 13 further comprising an applicator adapted to be used for inserting said removable absorber into a designated position inside said absorptive product through said access port.

21. An absorptive product as in claim 1, claim 2, claim 3, claim 7, claim 8, or claim 13 wherein said removable absorber has a handle adapted to be used when removing said removable absorber through said access port.

22. An absorptive product as in claim 1, claim 2, claim 3, claim 7, claim 8, or claim 13 wherein said front absorber contains more than 50 wt % of a super-absorbent polymer.

23. An absorptive product as in claim 22 wherein said front absorber comprises a non-woven base material and a mixture of a super-absorbent polymer and microfibril cellulose.

24. An absorptive product as in claim 22 wherein said rear absorber contains less than 10 wt % of a super-absorbent polymer.

25. An absorptive product as in claim 22 wherein said removable absorber comprises a hydrolyzable material.

* * * * *

UNITED STATES PATENT AND TRADEMARK OFFICE
CERTIFICATE OF CORRECTION

| | |
|---|---|
| PATENT NO. | : 7,175,613 B2 |
| APPLICATION NO. | : 10/394070 |
| DATED | : February 13, 2007 |
| INVENTOR(S) | : Katsuhiko Sugiyama et al. |

It is certified that error appears in the above-identified patent and that said Letters Patent is hereby corrected as shown below:

Title page, item "(73) Assignee:" add --Japan Absorbent Technology Institute, Tokyo, Japan--.

Signed and Sealed this

Twenty-ninth Day of May, 2007

JON W. DUDAS
*Director of the United States Patent and Trademark Office*